United States Patent
Lei et al.

(10) Patent No.: US 12,054,562 B2
(45) Date of Patent: Aug. 6, 2024

(54) CELL-PERMEABLE INHIBITORY AGENT AND METHODS OF USE THEREOF IN TREATMENT OF COGNITIVE AND MOOD DISORDERS

(71) Applicant: The Governing Council of the University of Toronto, Toronto (CA)

(72) Inventors: Gang Lei, Toronto (CA); Beverley Anne Orser, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 398 days.

(21) Appl. No.: 17/205,311

(22) Filed: Mar. 18, 2021

(65) Prior Publication Data
US 2021/0284692 A1 Sep. 16, 2021

Related U.S. Application Data

(63) Continuation of application No. 16/063,003, filed as application No. PCT/CA2016/051496 on Dec. 16, 2016, now Pat. No. 10,981,954.

(60) Provisional application No. 62/268,137, filed on Dec. 16, 2015.

(51) Int. Cl.
| | |
|---|---|
| *C07K 7/08* | (2006.01) |
| *A61K 9/00* | (2006.01) |
| *A61K 38/00* | (2006.01) |
| *A61K 38/08* | (2019.01) |
| *A61K 38/10* | (2006.01) |
| *A61P 25/00* | (2006.01) |
| *C07K 7/06* | (2006.01) |
| *C07K 14/005* | (2006.01) |
| *C07K 14/47* | (2006.01) |
| *C07K 16/18* | (2006.01) |
| *C07K 14/705* | (2006.01) |

(52) U.S. Cl.
CPC .............. *C07K 7/08* (2013.01); *A61K 9/0019* (2013.01); *A61K 38/08* (2013.01); *A61K 38/10* (2013.01); *A61P 25/00* (2018.01); *C07K 7/06* (2013.01); *C07K 14/005* (2013.01); *C07K 14/47* (2013.01); *C07K 16/18* (2013.01); *A61K 38/00* (2013.01); *C07K 14/705* (2013.01); *C07K 2319/10* (2013.01)

(58) Field of Classification Search
CPC .......... C07K 7/08; C07K 7/06; C07K 14/005; C07K 14/47; C07K 2319/10; A61K 38/08; A61K 38/10; A61P 25/00
See application file for complete search history.

(56) References Cited

U.S. PATENT DOCUMENTS

| | | |
|---|---|---|
| 7,745,391 B2 | 6/2010 | Mintz |
| 10,891,954 B2 | 4/2021 | Orser |
| 2013/0302352 A1 | 11/2013 | Orser |

OTHER PUBLICATIONS

Aarts, M., Liu, Y., Liu, L., Besshoh, S., Arundine, M., Gurd, J.W., Wang, Y-T., Salter, M.W., Tymianski, M., "Treatment of Ischemic Brain Damage by Perturbing NMDA Receptor—PSD-95 Protein Interactions", Science, Oct. 25, 2002, vol. 298, Issue 5594, pp. 846-850.

Antunes, M., Biala, G., "The novel object recognition memory: neurobiology, test procedure, and its modifications", Cognitive Processing, May 2012, vol. 13, Issue 2, pp. 93-110.

Asai, Y., Takano, A., Ito, H., Okubo, Y., Matsuura, M., Otsuka, A., Takahashi, H., Ando, T., Ito, S., Arakawa, R., Asai, K., Suhara, T., "GABAA/Benzodiazepine receptor binding in patients with schizophrenia using [11C]Ro15-4513, a radioligand with relatively high affinity for α5 subunit", ScienceDirect, Schizophrenia Research 99 (2008), pp. 333-340.

Atack, J.R., Alder, L., Cook, S.M., Smith, A.J., McKernan, R.M., "In vivo labelling of α5 subunit-containing GABA A receptors using the selective radioligand(3H)L-655,708", Neuropharmacology, Aug. 1, 2005, vol. 49, Issue 2, pp. 220-229.

Atack, J.R., "Preclinical and clinical pharmacology of the GABAA receptor α5 subtype-selective inverse agonist α5IA", Pharmacology & Therapeutics, Jan. 2010, vol. 125, Issue 1, pp. 11-26.

Aubel, T., Kaufman, R., Montalmant, F., Kritzer, M.F., "Effects of gonadectomy and hormone replacement on a spontaneous novel object recognition task in adult male rats", Hormones and Behavior, Jul. 2008, vol. 54, Issue 2, pp. 244-252.

Belelli, D., Lambert, J.L., Peters, J.A., Wafford, K., Whiting, P.J., "The interaction of the general anesthetic etomidate with the γ-aminobutyric acid type A receptor is influenced by a single amino acid", Proceedings of the National Academy of Sciences USA, Sep. 30, 1997, vol. 94, Issue 20, pp. 11031-11036.

(Continued)

*Primary Examiner* — Olga N Chernyshev

(74) *Attorney, Agent, or Firm* — Leydig, Voit & Mayer, Ltd.

(57) ABSTRACT

The present application provides an inhibitory compound, such as a peptide, and methods for using the inhibitory compound in the treatment, diagnosis or monitoring of cognitive and mood disorders that are typically associated with memory loss and/or loss of executive function. In one example, the inhibitory compound is a peptide that mimics the N-terminal sequence of the intracellular loop of α5 subunit of α5GABA$_A$ receptors. Also provided are compositions and methods for treating a disorder associated with memory loss or loss of executive function. The therapeutic method comprises the step of inhibiting binding of radixin to α5GABA$_A$ receptors, for example, by administration of the presently described inhibitory compound or peptide.

15 Claims, 16 Drawing Sheets

Specification includes a Sequence Listing.

(56) References Cited

OTHER PUBLICATIONS

Borota, D., Murray, E., Keceli, G., Chang, A., Watabe, J.M., Ly, M., Toscano, J.P., Yassa, M.A., "Post-study caffeine administration enhances memory consolidation in humans", Nature Neuroscience, Feb. 2014, vol. 17, Issue 2, pp. 201-203.
Botta, P., Demmou, L., Kasugai, Y., Markovic, M., Xu, C., Fadok, J.P., Lu, T., Poe, M.M., Xu, L., Cook, J.M., Rudolph, U., Sah, P., Ferraguti, F., Luethi, A., "Regulating anxiety with extrasynaptic inhibition", Nature Neuroscience, Oct. 2015, vol. 18, Issue 10, pp. 1493-1500.
Botton, P.H., Costa, M.S., Ardais, A.P., Mioranzza, S., Souza, D.O., Teixeira Da Rocha, J.B., Porciuncula, L.O., "Caffeine prevents disruption of memory consolidation in the inhibitory avoidance and novel object recognition tasks by scopolamine in adult mice", Behavioural Brain Research, Dec. 25, 2010, vol. 214, Issue 2, pp. 254-259.
Brady, M.L., Jacob, T.C., "Synaptic localization of α5 GABA (A) receptors via gephyrin interaction regulates dendritic outgrowth and spine maturation", Developmental Neurobiology, Nov. 2015, vol. 75, Issue 11, pp. 1241-1251.
Braudeau, J., Delatour, B., Duchon, A., Pereira, P.L., Dauphinot, L., De Chaumont, F., Olivo-Marin, J-C., Dodd, R.H., Herault, Y., Potier, M-C., "Specific targeting of the GABA-A receptor α5 subtype by a selective inverse agonist restores cognitive deficits in Down syndrome mice", Journal of Psychopharmacology, 2011, vol. 25, Issue 8, pp. 1030-1042.
Caraiscos, V.B., Elliott, E.M., You-Ten, K.E., Cheng, V.Y., Belelli, D., Newell, J.G., Jackson, M.F., Ambert, J.J., Rosahl, T.W., Wafford, K.A., MacDonald, J.F. Orser, B.A., "Tonic inhibition in mouse hippocampal CA1 pyramidal neurons is mediated by α5 subunit-containing γ-aminobutyric acid type A receptors", Proceedings of the National Academy of Sciences USA, Mar. 9, 2004, vol. 101, Issue 10, pp. 3662-3667.
Choii, G., Ko, J., "Gephyrin: a central GABAergic synapse organizer", Literature Review, Experimental and Molecular Medicine, Mar. 2015, vol. 47, Issue 3, 8 pages.
Clarkson, A.N., Huang, B.S., MacIsaac, S.E., Mody, I., Carmichael, S.T., "Reducing excessive GABAergic tonic inhibition promotes post-stroke functional recovery", Nature, Nov. 11, 2010, vol. 468, Issue 7321, pp. 305-309.
Costa, M.S., Botton, P.H., Mioranzza, S., Souza, D.O., Porciuncula, L.O., "Caffeine prevents age-associated recognition memory decline and changes brain-derived neurotrophic factor and tirosine kinase receptor (TrkB) content in mice", Neuroscience, Jun. 2, 2008, vol. 153, Issue 4, pp. 1071-1078.
Craddock, N., Owen. M.J., "The beginning of the end for the Kraepelinian dichotomy", British Journal of Psychiatry, May 2005, vol. 186, pp. 364-366.
Crestani, F., Keist, R., Fritschy, J-M, Benke, D., Vogt, K., Prut, L., Bluethmann, H., Moehler, H., Rudolph, U., "Trace fear conditioning involves hippocampal alpha5 GABA(A) receptors", Proceedings of the National Academy of Sciences USA, Jun. 25, 2002, vol. 99, Issue 13, pp. 8980-8985.
Damgaard, T., Larsen, D.B., Hansen, S.L., Grayson, B., Neill, J.C., Plath, N., "Positive modulation of alpha-amino-3-hydroxy-5-methyl-4-isoxazolepropionic acid (AMPA) receptors reverses sub-chronic PCP-induced deficits in the novel object recognition task in rats", Behavioural Brain Research, Feb. 11, 2010, vol. 207, Issue 1, pp. 144-150.
Fan, X., Jin, W.Y., Lu, J., Wang, J., Wang, Y.T., "Rapid and reversible knockdown of endogenous proteins by peptide-directed lysosomal degradation", Nature Neuroscience, Mar. 2014, vol. 17, Issue 3, pp. 471-480.
Fatemi, S.H., Reutiman, T.J., Folsom, T.D., Rooney, R.J., Patel, D.H., Thuras, P.D., "mRNA and protein levels for GABA Aα4, α5, β1 and GABABR1 receptors are altered in brains from subjects with autism", Journal of Autism and Developmental Disorders, Jun. 2010, vol. 40, Issue 6, pp. 743-750.

Fischell, J., Van Dyke, A.M., Kvarta, M.D., Legates, T.A., Thompson, S.M., "Rapid Antidepressant Action and Restoration of Excitatory Synaptic Strength After Chronic Stress by Negative Modulators of Alpha5-Containing GABAA Receptors", Neuropsychopharmacology, Oct. 2015, vol. 40, Issue 11, pp. 2499-2509.
Forman, S.A., "Clinical and Molecular Pharmacology of Etomidate", Anesthesiology, Mar. 2011, vol. 114, Issue 3, pp. 695-707.
Gill, K.M., Lodge, D.J., Cook, J.M., Aras, S., Grace, A.A., "A Novel a5GABAAR-Positive Allosteric Modulator Reverses Hyperactivation of the Dopamine System in the MAM Model of Schizophrenia", Neuropsychopharmacology, May 2011, vol. 36, Issue 9, pp. 1903-1911.
Goulart, B.K., De Lima, M.N.M., De Farias, C.B., Reolon, G.K., Almeida, V.R., Quevedo, J., Kapczinski, F., Schroeder, N., Roesler, R., "Ketamine impairs recognition memory consolidation and prevents learning-induced increase in hippocampal brain-derived neurotrophic factor levels", Neuroscience, Jun. 2, 2010, vol. 167, Issue 4, pp. 969-973.
Hammond, R.S., Tull, L.E., Stackman, R.W., "On the delay-dependent involvement of the hippocampus in object recognition memory", Neurobiology of Learning and Memory, Jul. 2004, vol. 82, Issue 1, pp. 26-34.
Hausrat, T.J., Muhia, M., Gerrow, K., Thomas, P., Hirdes, W., Tsukita, S., Heisler, F.F., Herich, L., Dubroqua, S., Breiden, P., Feldon, J., Schwarz, J.R., Yee, B.K., Smart, T.G., Triller, A., Kneussel, M., "Radixin regulates synaptic GABAA receptor density and is essential for reversal learning and short-term memory", Nature Communications, Apr. 20, 2015, vol. 6:6872, pp. 1-17.
Heishman, S.J., Kleykamp, B.A., Singleton, E.G., "Meta-analysis of the acute effects of nicotine and smoking on human performance", Psychopharmacology, Jul. 2010, vol. 210, Issue 4, pp. 453-469.
Herring, N.R., Schaefer, T.L., Gudelsky, G.A., Vorhees, C.V., Williams, M.T., "Effect of (+)-Methamphetamine on Path Integration Learning, Novel Object Recognition, and Neurotoxicity in Rats", Psychopharmacology, Sep. 2008, vol. 199, Issue 4, pp. 637-650.
Ingvar, M., Ambros-Ingerson, J., Davis, M., Granger, R., Kessler, M., Rogers, G.A., Schehr, R.S., Lynch, G., "Enhancement by an Ampakine of Memory Encoding in Humans", Experimental Neurology, Aug. 1997, vol. 146, Issue 2, pp. 553-559.
Jo, S., Yarishkin, O., Hwang, Y.J., Chun, Y.E., Park, M., Woo, D.H., Bae, J.Y., Kim, T., Lee, J., Chun, H., Park, H.J., Lee, D.Y., Hong, J., Kim, H.Y, Oh, S-J., Park. S.J., Lee, H., Yoon, B-E., Kim, Y-S., Jeong, Y., Shim, I., Bae, Y.C., Cho, J., Kowall, N.W., Ryu, H., Hwang, E., Kim, D., Lee, C.J., "GABA from reactive astrocytes impairs memory in mouse models of Alzheimer's disease", Nature Medicine, Aug. 2014, vol. 20, Issue 8, pp. 886-896.
Leite, D.M., Barbu, E., Pilkington, G.J., Lalatsa, A., "Peptide Self-Assemblies for Drug Delivery", Current Topics in Medicinal Chemistry, 2015, vol. 15, Issue 22, pp. 2277-2289.
Loebrich, S., Baehring, R., Katsuno, T., Tsukita, S., Kneussel, M., "Activated radixin is essential for GABAA receptor α5 subunit anchoring at the actin cytoskeleton", The Embo Journal, Mar. 8, 2006, vol. 25, Issue 5, pp. 987-999.
Luescher, B., Keller, C.A., "Regulation of GABAA receptor trafficking, channel activity, and functional plasticity of inhibitory synapses", Pharmacology & Therapeutics, Jun. 2004, vol. 102, Issue 3, pp. 195-221.
Martin, L.J., Zurek, A.A., MacDonald, J.F., Roder, J.C., Jackson, M.F., Orser, B.A., "5GABAA Receptor Activity Sets the Threshold for Long-Term Potentiation and Constrains Hippocampus-Dependent Memory", The Journal of Neuroscience, Apr. 2010, vol. 30, Issue 15, pp. 5269-5282.
Martinez-Cue, C., Delatour, B., Potier, M-C., "Treating enhanced GABAergic inhibition in Down syndrome: Use of GABA α5-selective inverse agonists", Neuroscience & Biobehavioral Reviews, Oct. 2014, vol. 46, Part 2, pp. 218-227.
Mendez, M.A., Horder, J., Myers, J., Coghlan, S., Stokes, P., Erritzoe, D., Howes, O., Lingford-Hughes, A., Murphy, D., Nutt, D., "The brain GABA-benzodiazepine receptor alpha-5 subtype in

(56) References Cited

OTHER PUBLICATIONS autism spectrum disorder. A pilot [11C]Ro15-4513 positron emission tomography study", Neuropharmacology, May 2013, vol. 68, pp. 195-201.

Milic, M., Timic, T., Joksimovic, S., Biawat, P., Rallapalli, S., Divljakovic, J., Radulovic, T., Cook, J. M., Savic, M.M., "PWZ-029, an inverse agonist selective for α5 GABAA receptors, improves object recognition, but hot water-maze memory in normal and scopolamine-treated rats", Behavioural Brain Research, Mar. 15, 2013, vol. 241, pp. 206-213.

Moehler, H., "Cognitive enhancement by pharmacological and behavioral interventions: the murine Down syndrome model", Biochemical Pharmacology, Oct. 15, 2012, vol. 84, Issue 8, pp. 994-999.

Nanfaro, F., Cabrera, R., Bazzocchini, V., Laconi, M., Yunes, R., "Pregnenolone sulfate infused in lateral septum of male rats impairs novel object recognition memory", Pharmacological Reports, Mar.-Apr. 2010, vol. 62, Issue 2, pp. 265-272.

Nutt, D., "GABAA Receptors: Subtypes, Regional Distribution, and Function", Literature Review, Journal of Clinical Sleep Medicine, May 2006, vol. 2, Issue 2, pp. S7-11.

Nutt, D.J., Besson, M., Wilson, S.J., Dawson, G.R., Lingford-Hughes, A.R., "Blockade of alcohol's amnestic activity in humans by an α5 subtype benzodiazepine receptor inverse agonist", Neuropharmacology, Dec. 2007, vol. 53, Issue 7, pp. 810-820.

Olsen, R.W., Sieghart, W., "International Union of Pharmacology. LXX. Subtypes of γ-Aminobutyric AcidA Receptors: Classification on the Basis of Subunit Composition, Pharmacology, and Function. Update", Pharmacological Reviews, Sep. 2008, vol. 60, Issue 3, pp. 243-260.

Papadimitriou, G.N., Dikeos, D.G., Karadima, G., Avramopoulos, D., Daskalopoulou, E.G., Vassilopoulos, D., Stefanis, C.N., "Association between the GABA(A) receptor α5 subunit gene locus (GABRA5) and bipolar affective disorder", American Journal of Medical Genetics—Neuropsychiatric Genetics, Feb. 1998, vol. 81, Issue 1, pp. 73-80.

Papadimitriou, G., Dikeos, D., Daskalopoulou, E., Karadima, G., Avramopoulos, D., Contis, C., Stefanis, C., "Association between GABA-A Receptor Alpha 5 Subunit Gene Locus and Schizophrenia of a Later Age of Onset", Neuropsychobiology, Mar. 2001, vol. 43, Issue 3, pp. 141-144.

Pettingill, P., Kramer, H.B., Coebergh, J.A., Pettingill, R., Maxwell, S., Nibber, A., Malaspina, A., Jacob, A., Irani, S.R., Buckley, C., Beeson, D., Lang, B., Waters, P., Vincent, A., "Antibodies to GABAA receptor α1 and γ2 subunits: Clinical and serologic characterization", Neurology, Mar. 24, 2015, vol. 84, Issue 12, pp. 1233-1241.

Potier, M-C., Braudeau, J., Dauphinot, L., Delatour, B., "Reducing Gabaergic Inhibition Restores Cognitive Functions in a Mouse Model of Down Syndrome", CNS & Neurological Disorders—Drug Targets, 2014, vol. 13, Issue 1, pp. 8-15.

Prut, L., Prenosil, G., Willadt, S., Vogt, K., Fritschy, J.-M., Crestani, F., "A reduction in hippocampal GABAA receptor α5 subunits disrupts the memory for location of objects in mice", Genes, Brain and Behavior, 2010, vol. 9, pp. 478-488.

Rudolph, U., Moehler, H., "GABAA Receptor Subtypes: Therapeutic Potential in Down Syndrome, Affective Disorders, Schizophrenia, and Autism", Annual Review of Pharmacology and Toxicology, Jan. 2014, vol. 54, pp. 483-507.

Saab, B.J., MacLean, A.J.B., Kanisek, M., Zurek, A.A., Martin, L.J., Roder, J.C., Orser, B.A., "Short-term Memory Impairment after Isoflurane in Mice Is Prevented by the α5 γ-Aminobutyric Acid Type A Receptor Inverse Agonist L-655,708", Anesthesiology, Nov. 2010, vol. 113, No. 5, pp. 1061-1071.

Savic, M.M., Clayton, T., Furtmueller, R., Gavrilovic, I., Samardzic, J., Savic, S., Huck, S., Sieghart, W., Cook, J.M., "PWZ-029, a compound with moderate inverse agonist functional selectivity at GABAA receptors containing α5 subunits, improves passive, but not active, avoidance learning in rats", Brain Research, May 7, 2008, vol. 1208, pp. 150-159.

Schindler, A.G., Li, S., Chavkin, C., "Behavioral Stress May Increase the Rewarding Valence of Cocaine-Associated Cues Through a Dynorphin/κ-Opioid Receptor-Mediated Mechanism without Affecting Associative Learning or Memory Retrieval Mechanisms", Neuropsychopharmacology, Aug. 2010, vol. 35, Issue 9, pp. 1932-1942.

Schroeder, N., O'Dell, S.J., Marshall, J.F., "Neurotoxic methamphetamine regimen severely impairs recognition memory in rats", Synapse, Aug. 2003, vol. 49, Issue 2, pp. 89-96.

Serantes, R., Arnalich, F., Figueroa, M., Salinas, M., Andres-Mateos, E., Codoceo, R., Renart, J., Matute, C., Cavada, C., Cuadrado, A., Montiel, C., "Interleukin-1β Enhances GABAA Receptor Cell-surface Expression by a Phosphatidylinositol 3-Kinase/Akt Pathway", Journal of Biological Chemistry, May 26, 2006, vol. 281, Issue 21, pp. 14632-14643.

Soh, M.S., Lynch, J.W., "Selective Modulators of α5-Containing GABAA Receptors and their Therapeutic Significance", Current Drug Targets, Mar. 2015, vol. 16:999, pp. 1-26.

Tian, S., Pan, S., You, Y., "Nicotine enhances the reconsolidation of novel object recognition memory in rats", Pharmacology, Biochemistry and Behavior, Feb. 2015, vol. 129, pp. 14-18.

Tyagarajan, S.K., Fritschy, J-M, "Gephyrin: a master regulator of neuronal function?", Nature Reviews Neuroscience, Feb. 2014, vol. 15, pp. 141-156.

Varley, J., Vincent, A., Irani, S.R., "Clinical and experimental studies of potentially pathogenic brain-directed autoantibodies: current knowledge and future directions", Journal of Neurology, Apr. 2015, vol. 262, Issue 4, pp. 1081-1095.

Walf, A.A., Koonce, C., Manley, K., Frye, C.A., "Proestrous compared to diestrous wildtype, but not estrogen receptor beta knockout, mice have better performance in the spontaneous alternation and object recognition tasks and reduced anxiety-like behavior in the elevated plus and mirror maze", Behavioural Brain Research, Jan. 23, 2009, vol. 196, Issue 2, pp. 254-260.

Wu, Z., Guo, Z., Gearing, M., Chen, G., "Tonic inhibition in dentate gyrus impairs long-term potentiation and memory in an Alzhiemer's disease model", Nature Communications, 2014, vol. 5:4159, pp. 1-12.

Yee, B.K., Hauser, J., Dolgov, V.V., Keist, R., Moehler, H., Rudolph, U., Feldon, J., "GABAA receptors containing the α5 subunit mediate the trace effect in aversive and appetitive conditioning and extinction of conditioned fear", European Journal of Neuroscience, Oct. 2004, vol. 20, Issue 7, pp. 1928-1936.

Zurek, A.A., Bridgwater, E.M., Orser, B.A., "Inhibition of α5 γ-Aminobutyric Acid Type A Receptors Restores Recognition Memory After General Anesthesia", Anesthesia and analgesia, Apr. 2012, vol. 114, Issue 4, pp. 845-855.

Zurek, A.A., Yu, J., Wang, D.S., Haffey, S.C., Bridgwater, E.M., Lecker, P.A., Lei, G., Chang, T., Salter, E.W., Orser, B.A., "Sustained increase in 5GABAA receptor function impairs memory after anesthesia", The Journal of Clinical Investigation, Dec. 2014, vol. 124, Issue 12, pp. 5437-5441.

Broadbent N.J. et al. (2004) Spatial memory, recognition memory and the hippocampus, Proc. Nat'l Acad. Sciences (PNAS) 101:14515-14520 (publisher: The National Academy of Sciences of the USA).

Dix S. L. & Aggleton J.P. (1999) "Extending the spontaneous preference test of recognition: evidence of object-location and object-context recognition," Behavioural Brain Research, 99:191-200. (publisher: Elsevier).

Martinez-Cué C. et al. (2013) "Reducing $GABA_A$ α5 Receptor-Mediated Inhibition Rescues Functional and Neuromorphological Deficits in a Mouse Model of Down Syndrome," Journal of Neuroscience 33(9):3953-3966 (publisher: The Society of Neuroscience).

Zurek AA, Kemp SW, Aga Z, et al. (2016) "a5$GABA_A$ receptor deficiency causes autism-like behaviors." Ann Clin Transl Neurol 2016;3:392-8 (publisher: American Neurological Association).

SEQUENCE LISTING

```
<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Asn Tyr Phe Thr Lys Arg Gly Trp Ala Trp Asp Gly Lys Lys Ala Leu
1               5                   10                  15

<210> SEQ ID NO 2
<211> LENGTH: 12
<212> TYPE: PRT
<213> ORGANISM: Homo sapiens

<400> SEQUENCE: 2

Lys Arg Gly Trp Ala Trp Asp Gly Lys Lys Ala Leu
1               5                   10

<210> SEQ ID NO 3
<211> LENGTH: 10
<212> TYPE: PRT
<213> ORGANISM: Homo sapiens

<400> SEQUENCE: 3

Gly Trp Ala Trp Asp Gly Lys Lys Ala Leu
1               5                   10

<210> SEQ ID NO 4
<211> LENGTH: 8
<212> TYPE: PRT
<213> ORGANISM: Homo sapiens

<400> SEQUENCE: 4

Ala Trp Asp Gly Lys Lys Ala Leu
1               5

<210> SEQ ID NO 5
```

```
<211> LENGTH: 16
<212> TYPE: PRT
<213> ORGANISM: Artificial Sequence
<220> FEATURE:
<223> OTHER INFORMATION: Scramble peptide

<400> SEQUENCE: 5

Thr Tyr Phe Gly Arg Lys Asn Ala Leu Trp Lys Ala Trp Lys Gly Asp
1               5                   10                  15

<210> SEQ ID NO 6
<211> LENGTH: 27
<212> TYPE: PRT
<213> ORGANISM: Homo sapiens

<400> SEQUENCE: 6

Tyr Gly Arg Lys Lys Arg Arg Gln Arg Arg Asn Tyr Phe Thr Lys
1               5                   10                  15

Arg Gly Trp Ala Trp Asp Gly Lys Lys Ala Leu
            20                  25

<210> SEQ ID NO 7
<211> LENGTH: 27
<212> TYPE: PRT
<213> ORGANISM: Artificial Sequence
<220> FEATURE:
<223> OTHER INFORMATION: Scramble peptide with TAT sequence

<400> SEQUENCE: 7

Tyr Gly Arg Lys Lys Arg Arg Gln Arg Arg Thr Tyr Phe Gly Arg
1               5                   10                  15

Lys Asn Ala Leu Trp Lys Ala Trp Lys Gly Asp
            20                  25

<210> SEQ ID NO 8
<211> LENGTH: 12
<212> TYPE: PRT
<213> ORGANISM: Homo sapiens

<400> SEQUENCE: 8

Asn Tyr Phe Thr Lys Arg Gly Trp Ala Trp Asp Gly
1               5                   10

<210> SEQ ID NO 9
<211> LENGTH: 6
<212> TYPE: PRT
<213> ORGANISM: Homo sapiens

<400> SEQUENCE: 9

Asp Gly Lys Lys Ala Leu
1               5

<210> SEQ ID NO 10
<211> LENGTH: 4
<212> TYPE: PRT
<213> ORGANISM: Homo sapiens

<400> SEQUENCE: 10

Lys Lys Ala Leu
1
```

CELL-PERMEABLE INHIBITORY AGENT AND METHODS OF USE THEREOF IN TREATMENT OF COGNITIVE AND MOOD DISORDERS

CROSS-REFERENCE TO RELATED APPLICATION(S)

This application is a continuation of U.S. application Ser. No. 16/063,003, filed Jun. 15, 2018, which is a 371 of International Application No. PCT/CA2016/051496, filed Dec. 16, 2016, which claims the benefit of U.S. Provisional Application No. 62/268,137, filed Dec. 16, 2015. Each of these applications is incorporated by reference herein in its entirety.

REFERENCE TO A SEQUENCE LISTING SUBMITTED VIA EFS-WEB

The ASCII text file of the sequence listing named "338747-60-18AUS_ST25" which is 3 kb in size is electronically submitted via EFS-Web herewith, is a part of the application as filed and is incorporated herein by reference in its entirety.

TECHNICAL FIELD

This disclosure relates to the field of therapies for the treatment or prevention of cognitive or mood disorders. More particularly, the present disclosure relates to treatment or prevention of cognitive and mood disorders using an inhibitory agent, such as a peptide, that targets $\alpha 5GABA_A$ receptor activity.

BACKGROUND

γ-Aminobutyric acid (GABA) is the major inhibitory neurotransmitter in the mammalian brain. The majority of GABA actions are mediated by type A GABA ($GABA_A$) receptors, which are ligand-gated anion channels. These ion channels are pentameric complexes that contain an integral chloride-permeable pore. Binding of GABA to the receptor activates the channel by opening the pore. This increases chloride permeability and typically reduces neuronal excitability. There are at least 19 different genes (Olsen & Sieghart, 2008) that encode the various subunits of the $GABA_A$ receptors. Most mature $GABA_A$ receptors are formed from two a subunits, two β subunits and a subunit that is γ, δ, ε, θ, π or ρ. The subunit composition of the receptors confers distinct pharmacological properties to the receptors and distinct patterns of distribution in terms of locations in the brain and subcellular expression patterns (Nutt 2006).

$GABA_A$ receptors are involved in a multitude of physiological processes and neurological disorders. An increase in GABAergic inhibition has been associated with cognitive disorders such as memory loss associated with aging, Alzheimer's disease, Down syndrome, Fragile X syndrome and postoperative cognitive dysfunction. Normalizing inhibitory neurotransmission may be of great therapeutic value in treating these disorders.

Pharmacological approaches that non-selectively target $GABA_A$ receptors and inhibit their function are not clinically useful because of the adverse pro-convulsant and anxiogenic properties of the drugs. However, a strategy that selectively targets a specific subtype of $GABA_A$ receptors, particularly if the receptor has a restricted pattern of expression, represents a promising therapeutic approach that has not previously been explored.

$\alpha 5GABA_A$ receptors are expressed in several brain regions but are predominantly in the hippocampus where they primarily localize to extrasynaptic regions of the neurons. These receptors generate a tonic inhibitory conductance that powerfully regulates neuronal excitability and network plasticity. Alterations in the activity and expression levels of $\alpha 5GABA_A$ receptors in experimental animal models modify memory, problem solving and mood-related behaviors. More specifically, an increase in $\alpha 5GABA_A$ receptors typically causes memory deficits, whereas a reduction in receptor function improves memory performance for certain types of hippocampus-dependent memory-related tasks (Caraiscos et al., 2004a; Martin et al., 2010).

Abnormal activity and dysregulation of $\alpha 5GABA_A$ receptors in humans has been implicated in multiple clinical disorders including age-related dementia, schizophrenia, Down syndrome, stroke and anesthetic-induced amnesia. These receptors also contribute to inflammation-induced injury in neuronal and non-neuronal structures, such as the lung and pancreas. As a result, drugs or compounds that allosterically modulate $\alpha 5GABA_A$ receptor function have been developed. Most of these drugs, acting as negative or positive allosteric modulators (so called NAMs and PAMs), showed potential therapeutic effects in animal models; however, to date, few have been successfully implemented in clinical trials. Low therapeutic efficacy, serious adverse side-effects and off-target toxicity (e.g., renal toxicity) in humans have limited the use of these compounds (Rudolph & Mohler 2014; Soh & Lync 2015). Several examples of these compounds are described below.

The negative allosteric modulator α5IA improves ethanol-induced impaired performance in healthy subjects (Nutt et al., 2007). However, a clinical trial that probed the effectiveness of α5IA in patients was stopped due to renal toxicity (Atack 2010). At high concentrations, α5IA also activates al subunit-containing $GABA_A$ receptors, an action that is predicted to cause undesirable sedation. Another negative allosteric inhibitor of $\alpha 5GABA_A$ receptors, L-655, 708, is 30-70 fold more selective for $\alpha 5GABA_A$ receptors. However, L-655,708 has a relatively low efficacy for reducing $\alpha 5GABA_A$ receptor function (Atack, et al., 2005). Finally, drugs that act as allosteric inhibitors often fail to differentiate $\alpha 5GABA_A$ receptors that are necessary for baseline or physiological functions (e.g., support memory processes such as memory erasing).

Other than NAMs, no alternative treatments are currently available to treat cognitive, mood and inflammation-induced dysfunctions that result from up-regulation of $\alpha 5GABA_A$ receptor function. As noted above, almost all of the compounds that have been developed, act as reversible allosteric modulators at the benzodiazepine-recognition domain of the receptor and reduce channel function. There remains widespread interest in developing pharmacological agents that reduce $\alpha 5GABA_A$ receptor function by alternative mechanisms.

Genetically manipulating Gabar5 gene expression has been used as an alternative approach to reduce $\alpha 5GABA_A$ receptor function and treatments based on this approach showed improvements in memory performance in animal models (Crestani, et al., 2002; Yee, et al., 2004; Prut et al., 2010). Recently, the roles of endogenous specific antibodies in psychiatric disorders have gained some attention (Varley et al., 2015; Pettingill et al., 2015). Pettingill et al (2015) reported that incubation of primary hippocampal neurons with GABA$_A$ receptor IgG1 sera reduced surface GABA$_A$ receptor membrane expression; however, any impactful utility of GABA$_A$ receptor antibodies in the IgG1 sera in physiological and pathological conditions has not yet been reported.

The above information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide a cell-permeable inhibitory agent and methods of use thereof in treatment of cognitive and mood disorders. In accordance with an aspect of the present application, there is provided an inhibitory compound that interrupts binding of radixin to α5GABA$_A$ receptors. In some embodiments, the inhibitory compound is an antibody, a peptide, a peptidomimetic or a small molecule. In a particular embodiment, the inhibitory compound is an isolated or synthetic peptide that binds to an α5 subunit binding domain on radixin or that binds to a radixin binding domain on an α5GABA$_A$ receptor.

In accordance with an aspect of the present application, there is provided an isolated or synthetic peptide comprising the sequence of SEQ ID NO: 4, a conservative variant thereof or a sequence having at least 80% homology with SEQ ID NO:4. Optionally, the peptide comprises the sequence of SEQ ID NO:3, SEQ ID NO:2, SEQ ID NO:1, or a conservative variant thereof. In accordance with another aspect of the application, there is provided a method for treatment or prevention of a cognitive or mood disorder characterized or associated with impairment of memory or executive function or both in a subject, wherein said method comprises administering to the subject an agent that interrupts binding of radixin to α5GABA$_A$ receptors. In some embodiments, the inhibitory agent is an antibody, a peptide, a peptidomimetic or a small molecule. Optionally, the agent is an antibody or a peptide, such as an isolated or synthetic peptide comprising the sequence of SEQ ID NO: 4, a conservative variant thereof or a sequence having at least 80% homology with SEQ ID NO:4. In another alternative, the agent is a peptide-biomimicking small molecule that mimics the activity of the isolated or synthetic peptide comprising the sequence of SEQ ID NO: 4 in interrupting the binding of radixin to α5GABA$_A$ receptors.

In accordance with another aspect of the application, there is provided a method for improving memory or executive function or both in a subject, wherein said method comprises administering to the subject an agent that interrupts binding of radixin to α5GABA$_A$ receptors. In some embodiments, the inhibitory agent is an antibody, a peptide, a peptidomimetic or a small molecule. Optionally, the agent is an antibody or a peptide, such as an isolated or synthetic peptide comprising the sequence of SEQ ID NO: 4, a conservative variant thereof or a sequence having at least 80% homology with SEQ ID NO:4. In another alternative, the agent is a peptide-biomimicking small molecule that mimics the activity of the isolated or synthetic peptide comprising the sequence of SEQ ID NO: 4 in interrupting the binding of radixin to α5GABA$_A$ receptors.

In accordance with another aspect of the application, there is provided a pharmaceutical composition for use in (i) treating or preventing a cognitive or mood disorder characterized or associated with impairment of memory or executive function or both; or (ii) improving memory or executive function or both, said composition comprising an inhibitory agent and a pharmaceutically acceptable carrier or excipient, wherein the inhibitory agent interferes with binding of radixin to α5GABA$_A$ receptors.

In accordance with another aspect of the application, there is provided a pharmaceutical composition comprising a peptide comprising the sequence of SEQ ID NO: 4, a conservative variant thereof or a sequence having at least 80% homology with SEQ ID NO:4. In accordance with another aspect of the application, there is provided a pharmaceutical composition comprising a small molecule biomimetic that mimics the activity of the isolated or synthetic peptide comprising the sequence of SEQ ID NO: 4 in interrupting the binding of radixin to α5GABA$_A$ receptors.

The foregoing and other objects, features, aspects and advantages of the present invention will become more apparent from the following detailed description, taken in conjunction with the accompanying drawings, which description is by way of example only.

BRIEF DESCRIPTION OF DRAWINGS

For a better understanding of the present invention, as well as other aspects and further features thereof, reference is made to the following description which is to be used in conjunction with the accompanying drawings, where:

FIG. 1A depicts the α5 subunit and radixin binding motif, and FIG. 1B illustrates how the small inhibitory peptide uncouples the interaction between radixin and α5 subunit;

FIG. 2A depicts an example of Western blot and co-immunoprecipitation experiments and FIG. 2B graphically depicts the quantified data summarised from 3 experiments (** P<0.01, ANOVA, one way, n=3);

FIG. 3A depicts an example of Western blot and co-immunoprecipitation experiments, and FIG. 3B graphically depicts the data quantified from four experiments (NS indicates no significance between these two groups);

FIG. 4A depicts an example of co-immunoprecipitation and Western blot experiments and FIG. 4B graphically depicts the data quantified from 4 experiments (P>0.05, t-test, n=4);

FIG. 9A shows the tonic current measured one day after treatment. FIG. 9B shows the quantified data (Statistical analysis was performed with one-way ANOVA followed by Newman-Keuls post hoc test, * P<0.05, ** P<0.01, n=10 for Ctrl, n=12 for Etom, n=13 for Etom+Pep, and n=11 for Etom+sPep);

FIG. 10A depicts an example of a Western blot from tissue lysate prepared from the hippocampus of adult mice (C57BL/6JxSvEv129) injected (i.p.) with 8 mg/kg of etomidate, and the results shown in FIG. 10B and FIG. 10C depict the effect of etomidate on radixin phosphorylation, and total radixin expression (the data was quantified from 3 separate experiments, * P<0.05, t-test, two-tailed test, n=3; NS stands for no significance).

FIG. 11A depicts an example of co-immunoprecipitation and Western blot experiments and the data quantified for α5 surface expression and FIG. 11B depicts an example of co-immunoprecipitation and Western blot experiments and the data quantified for total protein expression of α5 subunit (Data shown as Mean±SD, * P<0.05, t-test, two-tail, n=4);

(FIG. 16B) propofol (Prop, 3 µM); and (FIG. 16C) isoflurane (ISO, 250 µM) and sevoflurance (SEVO, 266 µM)) in neurons grown in co-cultures.

DETAILED DESCRIPTION

Definitions

Figure 1A:
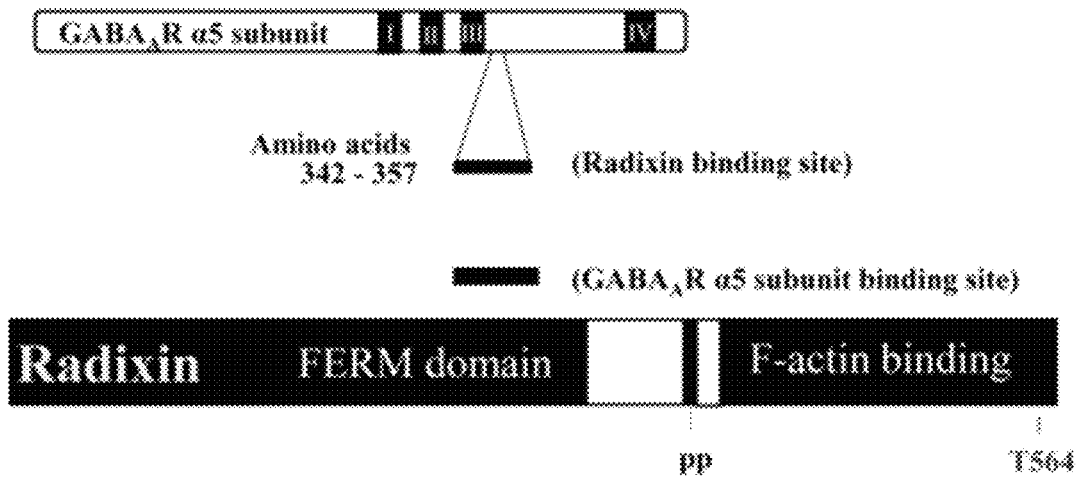
FIGS. 1A-1B depict the GABA$_A$ receptor α5 subunit binding domain for radixin according to an embodiment of the present invention.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising," as used herein will be understood to mean that the list following is non-exhaustive and may or may not include any other additional suitable items, for example one or more further feature(s), component(s) and/or ingredient(s) as appropriate.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "homology" is used herein to refer to the degree of similarity, or identity, between sequences, such as amino acid sequences. The term is not intended to require any shared ancestry among the sequences.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

An acid addition salt suitable for, or compatible with, the treatment of subjects is any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts can be formed and such salts can exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium, or barium hydroxide. Illustrative organic bases that form suitable salts include, but are not limited to, aliphatic, alicyclic or aromatic organic amines such as methylamine, trimethylamine and picoline, alkylammonias or ammonia. The selection of the appropriate salt will be known to a person skilled in the art.

The term "treating" or "treatment," as used herein and as is well understood in the art, means an approach for obtaining beneficial or desired results, including, for example, clinical results. Beneficial or desired clinical results can include, but are not limited to, alleviation or amelioration of one or more symptoms or conditions, diminishment of extent of disorder, stabilized (i.e., not worsening) state of disorder, delay or slowing of disorder progression, amelioration or palliation of the disorder, diminishment of the reoccurrence of the disorder, and remission (whether partial or total), whether detectable or undetectable. Treatment methods comprise administering to a subject a therapeutically effective amount of one or more of the compounds of the application and optionally consists of a single administration, or alternatively comprises a series of administrations. For example, the compounds of the application are administered at least once a week. However, in another embodiment, the compounds are administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, the age of the patient, the concentration, the activity of the compounds of the application, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration is required. For example, the compounds are administered to the subject in an amount and for a duration, sufficient to treat the patient.

As used herein, the term "effective amount" or "therapeutically effective amount" means an amount effective, at dosages and for periods of time necessary to achieve the desired result. For example, in the context of treating a disease, disorder or condition characterized by or associated with an over-abundance of $\alpha 5 GABA_A$ receptors on neuronal surfaces, an effective amount is an amount that, for example, reduces $\alpha 5 GABA_A$ receptor accumulation on neuronal surfaces compared to the $\alpha 5 GABA_A$ receptor accumulation without administration of the compound. Effective amounts can vary according to factors such as the stage or state of the disorder, age, sex and/or weight of the subject. The amount of a given compound that will correspond to such an amount will vary depending upon various factors, such as the given compound, the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective dose of a compound or composition of the application to a cell either in cell culture or in a subject.

The term "executive function," as used herein, refers to regulation or control of cognitive processes, such as, but not limited to working memory, reasoning, problem solving, planning, plan execution and task execution. Impairment of executive function associated with various cognitive and mood disorders. A "mood disorder" is a psychological disorder characterized by the elevation or lowering of a person's mood. Examples of mood disorders include, but are not limited to, depression and bipolar disorder.

The term "amino acid" refers to naturally occurring and non-naturally occurring amino acids, as well as amino acid analogs and amino acid mimetics that possess similar structural, chemical and/or functional characteristics to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Reference to an amino acid includes, for example, naturally occurring proteogenic L-amino acids as well as D-amino acids. Standard single letter or three letter notations have been used as follows:

A—Ala—alanine
C—Cys—cysteine
D—Asp—aspartic acid
E—Glu—glutamic acid
F—Phe—phenylalanine
G—Gly—glycine
H—His—histidine
I—Ile—Isoleucine
K—Lys—lysine
L—Leu—leucine
M—Met—methionine
N—Asn—asparagine
O—Pyl—pyrrolysine
P—Pro—proline
Q—Gln—glutamine
R—Arg—arginine
S—Ser—serine
T—Thr—threonine
U—Sec—selenocysteine
V—Val—valine
W—Trp—tryptophan
Y—Tyr—tyrosine.

The expression "amino acid analogs" as used herein, including in reference to non-naturally occurring amino acids and to modified naturally occurring amino acids, refers to compounds that have the same basic chemical structure as a naturally occurring amino acid, i.e., a carbon that is bound to a hydrogen, a carboxyl group, an amino group, and an R group, and includes, for example, homoserine, norleucine, methionine sulfoxide and methionine methyl sulfonium. Such analogs have modified R groups (such as, norleucine) or modified peptide backbones, but retain the same basic chemical structure as a naturally occurring amino acid. Amino acid analogs include chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homo-histidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of amino acid analogs, such as non-natural amino acids, including synthetic non-native amino acids or substituted amino acids, may be advantageous in a number of different ways.

The terms "polypeptide," "peptide" and "protein" refer to a polymer or oligomer of amino acid residues. The terms apply to naturally occurring amino acid polymers as well as amino acid polymers in which one or more amino acid residues are a non-naturally encoded amino acid. As used herein, the terms encompass amino acid chains of any length, including full length proteins, wherein the amino acid residues are linked by covalent peptide bonds. The polypeptides, peptides and proteins are written using standard sequence notation, with the nitrogen terminus being on the left and the carboxy terminus on the right.

The term "conservative amino acid substitutions" refers to all substitutions wherein the substituted amino acid has similar structural, chemical and/or functional properties with the corresponding amino acid in the reference sequence. By way of example, conservative amino acid substitutions involve substitution of one aliphatic or hydrophobic amino acid, e.g., alanine, valine, leucine, isoleucine, methionine, phenylalanine, or tryptophan with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, and glycine, with another. Conservative substitution tables providing functionally similar amino acids are known to those of ordinary skill in the art. Peptides comprising one or more conservative amino acid substitution are referred to herein as "conservative variants".

As used herein, the term "small molecule biomimetic" refers to a non-peptide compound that mimics the activity of a peptide, such as a non-peptide compound that mimics the inhibitory activity of the inhibitory peptide of the present application.

Compounds, Compositions and Methods of the Application

The present application provides an inhibitory compound, such as a peptide or a small molecule, and methods for using the inhibitory compound in the treatment, diagnosis or monitoring of cognitive and mood disorders, which are typically associated with memory loss and/or loss of executive function. In one example, the inhibitory compound is an inhibitory peptide that mimics the N-terminal sequence of the intracellular loop of α5 subunit, where a number of proteins, including scaffold proteins, signaling molecules and kinases, bind and generate a response. Consequently, the inhibitory peptide can also block intracellular signaling transduction.

Also provided are compositions and methods for treating a disorder associated with memory loss or loss of executive function. The therapeutic method comprises the step of inhibiting binding of radixin to α5GABA$_A$ receptors, for example, by administration of the presently described inhibitory compound or peptide.

The inhibitory compound and use thereof, as described herein, is efficacious and selective in the treatment of conditions characterized by or associated with memory and/or executive function loss or impairment, since the inhibitory compound preferentially reduces the number of "excess" receptors that occur under pathological conditions. The inhibitory compound (e.g., the inhibitory peptide) differs from currently employed pharmaceutical compounds or NAMs in terms of working mechanism; it inhibits α5GABA$_A$ receptor function through blocking the receptor trafficking and cell surface expression rather than via a non-specific binding or inhibitory effect.

Inhibitory Agent

The inhibitory agent, or compound, of the present application attenuates α5GABA$_A$ receptor function by interfering with the excessive trafficking of α5GABA$_A$ receptors to the cell surface that occurs under pathological conditions. More specifically, the present inhibitory agent, which can be an inhibitory peptide, targets and interferes with the signaling pathways that traffic receptors to the surface of neurons or maintain the receptors in the plasma membrane. This approach is effective since cell-surface trafficking is increased during a variety of pathological conditions, such as sepsis or after exposure to anesthetic drugs. The approach of using inhibitory peptides has been successfully used by others for a variety of other neurological and non-neurological disorders (Aarts et al., 2002; Fan et al., 2014; Leite et al., 2015), however, this approach has not been previously applied to attenuate α5GABA$_A$ receptor function.

Figure 1B:
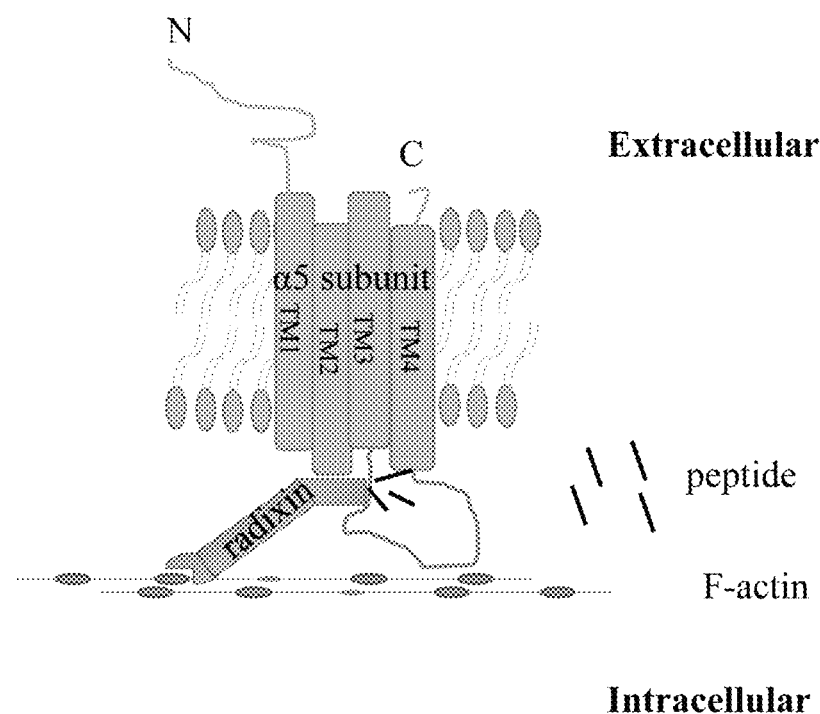

Radixin, a scaffolding protein located primarily at extrasynaptic sites of synapses, recruits and stabilizes α5GABA$_A$ receptors to the plasma membrane of the dendrites and the soma of neurons (FIG. 1B). Immunoimaging studies have shown that radixin and α5GABA$_A$ receptors co-localize. Also, studies that use pharmacological and genetic strategies to disrupt the interaction between radixin and α5GABA$_A$ receptors show a reduction in the tonic current that α5GABA$_A$ receptors generate (Loebrich et al, 2006; Hausrat et al., 2015). However, prior to the present studies utilizing the exemplary inhibitory peptide, there had been no demonstration or contemplation of any therapeutic benefit associated with such a disruption.

A specific binding domain on α5 subunit associates with radixin. As shown in FIG. 1A, this domain on the α5 subunit is a 16 amino-acid sequence located at positions 342 to 357 of the second intracellular loop (Loebrich et al, 2006). The radixin-binding domain of α5GABA$_A$ receptors is identical in man, mouse, rat, cow, dog, and monkey and shares 93% amino acid identity with the corresponding domain bird and fish (Loebrich et al, 2006). The present inventors have now designed and synthesized a specific inhibitory peptide that mimics the amino acid binding sequence of this α5 subunit (FIG. 1, Table 1). An aspect of the present application, therefore, is an agent, such as a peptide, that interferes with this binding of α5 subunit and thereby prevents the binding of α5GABA$_A$ receptors to radixin on cell plasma membrane. Administration of this inhibitory agent to a subject reduces the number of α5GABA$_A$ receptors that are expressed on the cell surface and/or interferes with α5GABA$_A$ receptor cluster formation and, consequently improves memory performance and/or executive function.

According to a particular aspect of this application, the inhibitory compound or agent is an antibody or antibody fragment that either binds to radixin or to the specific binding domain on the α5 subunit that associates with radixin, thereby disrupts, inhibits or eliminates the binding of radixin to α5GABA$_A$ receptors.

In another aspect of the present application, the inhibitory compound or agent is an inhibitory peptide that either binds to radixin or to the specific binding domain on the α5 subunit that associates with radixin, thereby disrupts, inhibits or eliminates the binding of radixin to α5GABA$_A$ receptors. In the examples provided below, an inhibitory peptide that specifically targeted the α5 subunit binding domain on radixin was used to interfere with this interaction and, thereby prevent cell surface expression of α5GABA$_A$ receptors. As would be readily appreciated by a worker skilled in the art, a peptide that binds to the reciprocal motif on the α5 subunit (i.e., the site where radixin binds to α5 subunits) will have a similar inhibitory affect.

According to a particular aspect of this application, the inhibitory compound or agent is an inhibitory peptide comprising a region that disrupts, inhibits or eliminates the binding of radixin to α5GABA$_A$ receptors. In one embodiment, the inhibitory agent comprises an eight amino acid peptide having the sequence of SEQ ID NO:4 (AWDGKKAL), or a conservative variant thereof. Alternatively, the inhibitory agent comprises a ten amino acid peptide having the sequence of SEQ ID NO:3 (GWAWDGKKAL), or a conservative variant thereof. In another alternative, the inhibitory agent comprises a twelve amino acid peptide having the sequence of SEQ ID NO:2 (KRGWAWDGKKAL). In another alternative, the inhibitory agent comprises a sixteen amino acid peptide having the sequence of SEQ ID NO:1 (NYFTKRGWAWDGKKAL).

The peptides disclosed herein can include peptides comprising an amino acid sequence having at least 80%, at least 85%, at least 90%, at least 95%, at least 96%, at least 97%, at least 98%, at least 99% of sequence homology with the peptide of SEQ ID NO:4 or a fragment thereof. In accordance with one embodiment, the inhibitory peptide comprises one or more amino acid analogue. In another embodiment, the peptide comprises a peptidomimetic. Examples of different amino analogues and peptidomimetics that can be included in the peptides and methods and compositions of the present application are enumerated above. The amino acid subunits are, in certain embodiments, linked by peptide bonds. In other embodiments, two or more amino acid subunits are linked by another type of bond, e.g. ester, ether, etc. In certain embodiments, peptidomimetics or amino acid analogues are incorporated into the peptide in order to reduce or eliminate proteolytic enzyme or protease susceptibility and improve stability of the peptide in vivo. In an alternative embodiment, the peptide is cyclized (between side chains or the termini of the peptide), again to reduce susceptibility to proteolytic enzymes or proteases and to improve stability. The incorporation of peptidomimetics or amino acid analogues, and/or the cyclization of the peptide is performed such that it does not reduce or significantly reduce the inhibitory effect of the peptide.

The peptides disclosed herein can be produced using conventional methods of peptide synthesis. Alternatively, the peptides can be produced using conventional methods of recombinant technology using nucleic acids that can express the inhibitory peptides from appropriate vectors and host cells, as are well known to workers skilled in the art.

Optionally the inhibitory peptide is beneficially modified by methods known to enhance passage of the molecule across cellular membranes and/or across the blood-brain barrier. For example, in one embodiment the peptide additionally comprises a polypeptide portion that facilitates transport of the peptide across cellular membranes. For example, the inhibitory peptide can comprise a cell-penetrating peptide (CPP), protein transduction domain (PTD), spontaneous membrane translocating peptide (SMTP) or the like. Examples of such peptide sequences are well known to those of skill in the art (see, for example, Bechara et al, 2013 and Macchi et al, 2015) and selection of the appropriate sequence can be made readily based on various factors, such as, for example, target tissue or cell type, type of subject, delivery composition and overall length of the inhibitory peptide.

Examples of sequences and transporters that are useful in facilitating transport of the peptide across cellular membranes are Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). These can be included as part of the inhibitory peptide, or can be formulated for administration together with the inhibitory peptide.

In some embodiments, the inhibitory peptide can be used for diagnostic purposes. For example, the peptide can be used as a binding peptide in assays to identify over or under expression of α5GABA$_A$ receptors, and/or to identify the over or under expression of radixin, and/or to explore association of radixin with α5GABA$_A$ receptors. In some examples of such diagnostic uses, the inhibitory peptide will additionally comprise a label or signal molecule useful for visualization of the peptide using imaging technologies. Selection of the appropriate label or signal molecule will depend on the imaging method and technology employed in the diagnostic method. The label can be, for example, a peptide sequence for binding by an antibody in an immunoassay, or a coloured molecule in the case of a colourimetric assay.

The present application further provides a diagnostic kit comprising a peptide comprising an amino acid sequence of SEQ ID NO:4, SEQ ID NO:3, SEQ ID NO:2, SEQ ID NO:1, a conservative variant of SEQ ID NO:4, SEQ ID NO:3, SEQ ID NO:2, or SEQ ID NO:1, or a peptide including an amino acid sequence having a sequence homology of 80% or greater to the amino acid sequence of SEQ ID NO:4; and instructions for use in a diagnostic assay or method.

In an alternative embodiment, the inhibitory peptide is used and/or adapted for use as an antigen for the production of antibodies, or antibody fragments, specific for the α5 subunit of α5GABA$_A$ receptors. As would be appreciated by a worker skilled in the art, such antibodies have particular utility as inhibitory agents, since they will function similarly to the present inhibitory peptide by masking or targeting the intracellular loop of the α5 subunit. Such antibodies will also have utility in binding methods or assays used to detect or quantify or visualize α5GABA$_A$ receptors.

According to a particular aspect of this application, the inhibitory compound or agent is a small molecule biomimetic of the inhibitory peptide of the present application (as described above). In particular, the present application further provides a small molecule biomimetic that binds to radixin or to the specific binding domain on the α5 subunit that associates with radixin, thereby disrupting, inhibiting, or eliminating the binding of radixin to the α5GABA$_A$ receptors.

Therapeutic Methods and Compositions

In accordance with another aspect, there is provided a method of treating a cognitive or mood disorder characterized by or associated with memory and/or executive function loss. The method comprises the step of administering to a subject an inhibitory agent to reduce α5GABA$_A$ receptor expression by inhibiting association of radixin with the α5GABA$_A$ receptor. In a particular example of this method, the inhibitor agent is an inhibitory peptide, such as a peptide comprising the sequence of SEQ ID NO:4, SEQ ID NO:3, SEQ ID NO:2 or SEQ ID NO:1.

Examples of cognitive or mood disorders treatable using the present method and compositions include, but are not limited to, cognitive deficits after surgery and/or anesthesia (Zurek et al, 2014; Zurek et al, 2012 and Saab et al, 2010), stroke (Clarkson et al, 2010), Alzheimer's Disease (Jo et al, 2014 and Wu et al, 2014), stress (Fischell et al, 2015), sepsis-associated encephalopathy (Serantes et al, 2006), Down syndrome (Mohler, 2012; Braudeau et al, 2011; Martinez-Cue et al, 2014; and Potier et al, 2014), schizophrenia (Asai et al, 2008; Craddock et al, 2005; Papadimitriou et al, 2001; Papadimitriou et al, 1998; and Gill et al, 2011), anxiety (Botta et al, 2015) and autism (Fatemi et al, 2010 and Mendez et al, 2013).

Also provided herein is the use of the present inhibitory agent in a method for preventing inflammation-induced dysfunctions or for modulation of the benzodiazepine-recognition domain of the α5GABA$_A$ receptor, for preventing α5GABA$_A$ receptor-related deficits after anesthesia and surgery or surgery or brain trauma, or acquired neurodegenerative disorders such as Alzheimer's disease. In another embodiment, there is provided the use of the present inhibitory agent in a method for treating side effects, such as memory deficits, associated with the use of certain GABAergic drugs, such as those that cause an allosteric up-regulation of the GABA receptor.

In the studies summarized in the following examples, the efficacy of the exemplary inhibitory peptide was demonstrated with behavioral deficits and biochemical and electrophysiological changes related to increased α5GABA$_A$ receptor function induced by a general anesthetic, etomidate. The injectable anesthetic etomidate (which increases the tonic current and thereby causes cognitive deficits) was selected for these studies. However, it is known that etomidate is only one of many drugs that increase GABA$_A$ receptor function. For example, the inhaled anesthetics sevoflurane and isoflurane, as well as the injectable anesthetic propofol and benzodiazepine midazolam similarly cause the sustained increase in tonic current. It is further known that inflammation also causes an increase in tonic current. The results provided in the Examples provide evidence that other anesthetic drugs such as desflurane and future anesthetics and benzodiazepines that increase GABA$_A$ receptor function will also cause cognitive deficits that can be treated with the inhibitory agent of the present application (e.g., an inhibitory peptide). Thus, the cognitive and mood deficits that are caused by these anesthetics, benzodiazepines and other drugs that increase GABA$_A$ receptor function can be prevented and treated with the inhibitory peptide. In summary, data provided in the Examples below provide the first evidence that these drugs that allosterically increase GABA$_A$ receptor activity, trigger a sustained increase in tonic current in neurons (as occurs with etomidate). Thus, cognitive and mood deficits cause by these drugs can be prevented and treated by the peptide.

The inhibitory agent of the present application can be administered in any manner that is medically acceptable. This can include injections, by parenteral routes such as intravenous, intravascular, intraarterial, subcutaneous, intramuscular, intratumor, intraperitoneal, intraventricular, intraepidural, intracranial, intranasal or others as well as nasal, or topical. Slow release administration is also specifically included in the invention, by such means as depot injections or erodible implants.

In one embodiment, the administration is parenteral injection, preferably intravenous, subcutaneous, intramuscular, intracranial or intraperitoneal. It is possible for the inhibitory agents of the present application to be administered as the raw chemical (e.g., the peptide alone), it is generally preferred for them to be administered in the form of a pharmaceutical formulation. The pharmaceutical formulations can be prepared by conventional techniques, such as described in Allen L V, Jr. Remington: The Science and Practice of Pharmacy. 22nd ed. London, UK: Pharmaceutical Press; 2012.

The term "pharmaceutically acceptable carrier" means one or more organic or inorganic ingredients, natural or synthetic, with which the inhibitory agent (e.g., inhibitory peptide) is combined to facilitate its application. A suitable carrier includes sterile saline although other aqueous and non-aqueous isotonic sterile solutions and sterile suspensions that are pharmaceutically acceptable are known to those of ordinary skill in the art.

The inhibitory agents of the present application can be formulated for parenteral administration and can be presented in unit dose form in ampoules, pre-filled syringes, small volume infusion or in multi-dose containers, optionally with an added preservative. The compositions can take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and can contain agents such as preserving, wetting, emulsifying or suspending, stabilizing and/or dispersing agents. Alternatively, the active ingredient can be in powder form, obtained by aseptic isolation of sterile solid or by lyophilisation from solution for constitution before use with a suitable vehicle, e.g., sterile, pyrogen-free water.

An "effective amount" refers to that amount that is capable of ameliorating or delaying progression of the cognitive or mood disorder. An effective amount can be determined on an individual basis and will be based, in part, on consideration of the symptoms to be treated and results sought. An effective amount can be determined by one of ordinary skill in the art employing such factors and using no more than routine experimentation.

In one aspect of the present application, there is provided a composition comprising an inhibitory agent as described above, which is optionally an inhibitory peptide comprising the sequence of SEQ ID NO:4, SEQ ID NO:3, SEQ ID NO:2, SEQ ID NO:1, any conservative variant thereof, or a sequence having at least 80% homology with SEQ ID NO:1. The composition can comprise a synthetic or isolated peptide as described herein, an isolated nucleic acid for expression of the inhibitory peptide as described herein, an expression vector encoding an inhibitory peptide as described herein, or a cell line expressing inhibitory peptides as described herein.

In one embodiment, there is provided a kit comprising a peptide comprising an amino acid sequence of SEQ ID NO:4, SEQ ID NO:3, SEQ ID NO:2, SEQ ID NO:1, a conservative variant of SEQ ID NO:4, SEQ ID NO:3, SEQ ID NO:2, or SEQ ID NO:1, or a peptide including an amino acid sequence having a sequence homology of 80% or greater to the amino acid sequence of SEQ ID NO:4; and instructions for at least one of administration dose, administration route, administration frequency, and indication of the peptide or composition.

In one embodiment the pharmaceutical composition or kit comprises the inhibitory agent (e.g., inhibitory peptide) as a pharmaceutical ingredient in combination with another composition for the treatment of cognitive or mood disorders, or for the prophylactic treatment of a subject facing the risk of developing a cognitive or mood disorder.

In one embodiment the inhibitory agent (e.g., inhibitory peptide) or composition is for the treatment of cognitive or mood disorders, or for the prophylactic treatment of a mammal facing the risk of developing a cognitive or mood disorder, and is combined with another pharmaceutical agent or composition for the treatment or prophylaxis of cognitive or mood disorders.

In particular, in one embodiment, the pharmaceutical composition further comprises a second active ingredient for treatment of cognitive or mood disorders, or for the prophylactic treatment of a subject facing the risk of developing a cognitive or mood disorder. In a related embodiment, the pharmaceutical composition further comprises a second active ingredient for improving memory function, for treating inflammation-induced dysfunctions or for modulation of the benzodiazepine-recognition domain of the α5GABA$_A$ receptor, for preventing α5GABA$_A$ receptor-related deficits after anesthesia and surgery or surgery or brain trauma, or acquired neurodegenerative disorders such as Alzheimer's disease.

Examples of ingredients that can be used as a second active ingredient to be administered before, during or after administration of the present inhibitory agent include, but are not limited to MRK-016, L-655,708, α5IA; R04938581, RG-1662, PWZ-029, TB-21007 and pyridazine and others (Milic et al. (2013), Savic et al (2008)).

As would be appreciated by those of skill in the art, the additional two or more active ingredients can be administered to a subject in combination with the presently provided inhibitory agent (e.g., inhibitory peptide) in the same composition or in a separate composition(s). When administered in a separate composition(s), the administration can be simultaneous with administration of the presently provided inhibitory agent (e.g., inhibitory peptide) or they can be administered at different times.

To gain a better understanding of the invention described herein, the following examples are set forth. It should be understood that these examples are for illustrative purposes only. Therefore, they should not limit the scope of this invention in any way.

EXAMPLES

Experimental Animals

All experimental procedures were approved by the Animal Care Committee of the University of Toronto (Toronto, Ontario, Canada). Adult mice (C57BL/6, 2-4 month old, male) and pregnant Swiss White mice were purchased from Charles River (Wilmington, MA, USA). Some adult mice (C57BL/6J×SvEv129, 2-4 month old, male) were also used and housed in the animal care facility of the University of Toronto. For in vivo experiments, the mice were treated with sedating doses of etomidate (8 mg/kg, i.p., single injection). Propylene glycol 35% (v/v) was used as the vehicle control as it is the solvent system for etomidate. To prevent potential hypoxia during the treatment, each mouse was placed in an air-tight acrylic chamber (27 cm×10 cm×10 cm) that was flushed with supplemental oxygen and medical air (70% air, 30% $O_2$) delivered at a flow of 1 L/min. The concentration of $O_2$ and $CO_2$ in the chamber were continuously monitored with a commercial gas analyzer (Datex Ohmeda, Mississauga, Ontari, Canada). To prevent hypothermia, the temperature of the chamber was maintained at 35 C.° with a heating blanket.

Synthesis of the Inhibitory Peptides

The inhibitory peptides were synthesized by BioMatik (Cambridge, ON, Canada). The sequences are confirmed by Mass Spectral analysis, and the purity of these peptides is over 95% as examined by HPLC.

Use of Etomidate

The prototypic injectable general anesthetic etomidate was studied in these examples. This drug is widely used in clinical practice, and is the most selective positive allosteric modulator of GABA$_A$Rs among the various intravenous and inhaled anesthetics (Forman 2011, Belelli et al. 1997). Also, etomidate causes minimal adverse hemodynamic effects (Forman (2011)). Thus, hemodynamic factors do not confound the interpretations of behavioral studies. Etomidate also offers the ease of injectable administration. For in vitro studies, a clinically-relevant concentration of etomidate (1 μM) was applied to the cell cultures. For in vivo studies, etomidate (8 mg/kg) was injected intraperitoneally (i.p.) at a sedative dose in a warmed and oxygenated environment.

The in vitro studies provided in the following Examples, also used etomidate to treat the astrocytes and neurons for in vitro studies. To extend these key findings to another major class of anesthetic, evidence that other anesthetics and a benzodiazepine increased in the tonic current in hippocampal neurons was obtained. Etomidate does not cause hemodynamic instability and is rapidly metabolized and eliminated. In addition, etomidate triggers the memory deficits by activating similar pathways to those activated by inflammatory processes. Thus, etomidate-induced memory loss is a model of cognitive deficits associated with inflammation resulting from disease or surgery. Other general anesthetics, including, for example, sevoflurane, isoflurane, propofol and sedative benzodiazepines, have now been found to increase the memory blocking tonic conductance in vitro (see FIG. 16). Thus, these additional anesthetics also cause memory deficits that can be prevented and treated with the inhibitory agent (e.g., inhibitory peptide) of the present application.

Example 1: Immunoprecipitation and Western Blotting Studies to Demonstrate Disruption of α5 Subunit-Radixin Interaction In this example, it was demonstrated, using co-immunoprecipitation (Co-IP) and Western blot (WB) analysis, that the inhibitory peptide prevented coupling between α5GABA$_A$ receptors and radixin.

The experiments used tissue lysate prepared from the hippocampus of adult mice (C57BL/6J×SvEv, 2-4 month old, male). Hippocampal tissue was homogenized in ice-cold RIPA buffer (20 mM Tris-HCL, pH 7.5, 150 mM NaCl, 1 mM Na2EDTA, 1 mM EGTA, 1% NP-40, 1% sodium deoxycholate, 2.5 mM sodium pyrophosphate, 1 mM β-glycerophosphate) supplemented with 1 mM sodium orthovanadate and 1% protease inhibitor cocktail and 1% phosphatase inhibitor cocktail (Roche Diagnostics, GmbH, Manheim Germany). The tissue lysate was subsequently spun at 14,000 rpm for 30 min with the Microfuge 22R Centrifuge (Beckman Coulter™, Brea, California, US). The supernatant was collected and frozen at −20 C°. The next day, the supernatant, after thawing, was re-centrifuged at 14,000 rpm for another 30 min to clear the potential undissolved or pellet substances. After spinning twice, the supernatant was collected for subsequent experiments.

For the immunoprecipitation experiment, the tissue lysate containing 500 mg protein (in 250 μl) was incubated with 20 μM (20 μl) of either the inhibitory peptide (SEQ ID NO:1) or scramble peptide (SEQ ID NO:5) without TAT sequence. One hour following the incubation, the antibodies (2-4 μg) against either α5 subunit (cat #sc—31417, Santa Cruz Biotechnology, Inc., 10410 Finnell St. Dallas, TX, 75220, USA) or radixin (cat #ab91312, Abcam Inc., c/o 913860, PO Box 4090 Stn A, Toronto, ON M5W 0E9), or 4 μg of non-specific IgG protein (cat #sc—2028, Santa Cruz Biotechnology, Inc., 10410 Finnell St. Dallas, TX, 75220, USA), were added to the lysate solution. After gently shaking overnight at 4° C., the immune complexes were precipitated with protein A/G plus-agarose beads (Santa Cruz Biotechnology, Inc., 10410 Finnell St. Dallas, TX, 75220, USA). Forty microliters of the A/G plus agarose beads were added to the immune complex solution and shaking gently for 2 h at 4° C. After spin with the microcentrifuge (Eppendorf Mini-Spin Plus, Marshall Scientific, 424 Route 125, Brentwood, NH 03833, USA), the immunoprecipitates were washed four times with ice-cold PBS, then resuspended in 2× Laemmli sample loading buffer containing 5% β-mercaptomethanol, and boiled for 5 min. These samples were subjected to Western blot experiment.

For Western blot, 40 μg (5-10 μl of tissue lysate) proteins or 10 μl of immunoprecipitates were separated by SDS-PAGE (10% acrylamide/bisacrylamide) and transferred at 4 C.° to the nitrocellulose membrane (BioTrace™ NT, Pall Corporation, 8780 Ely Rd, Pensacola, FL 32514, USA). The blotting analysis was performed by repeated stripping and successive probing with antibodies: anti-α5 (1:1000, cat #846-GASC, PhosphoSolutions Inc., 12635 East Montview Blvd., Aurora, CO 80045-7337, USA), anti-radixin (1:1000, cat #sc—6408, Santa Cruz Biotechnology, Inc., 10410 Finnell St. Dallas, TX, 75220, USA) and anti-pThr564-radixin (1:800, cat #3141, Cell Signaling Technology, New England Biolabs Ltd., 9 Carlow Court, Unit 3, Whitby, ON L1N 9T7, Canada). Other antibodies, including anti-gephyrin (cat #sc—25311), anti-GABA$_A$ receptor α1 (cat #sc—7348) and α2 (cat #sc—133602) subunits (Santa Cruz Biotechnology, Inc., 10410 Finnell St. Dallas, TX, 75220, USA) and anti β-actin (cat #A00730, GenScript, 860 Centennial Ave., Piscataway, NJ 08854, USA) were used. These results were analyzed with Molecular Imager (ChemiDocTMXRS+, Bio-Rad Inc.).

Figure 2A:
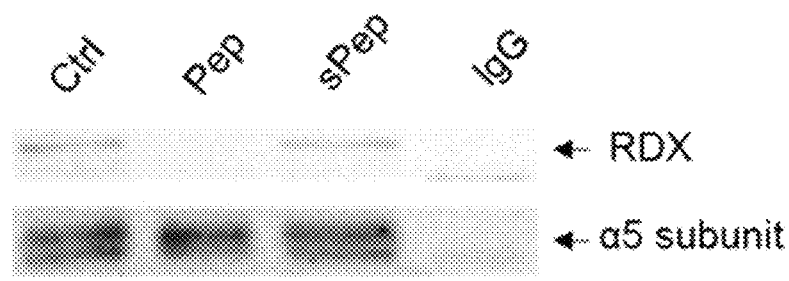
FIGS. 2A-2B depict the results of immunoprecipitation and Western Blot studies performed using anti-α5 and anti-pThr564-radixin antibodies according to an embodiment of the present invention.
Figure 2B:
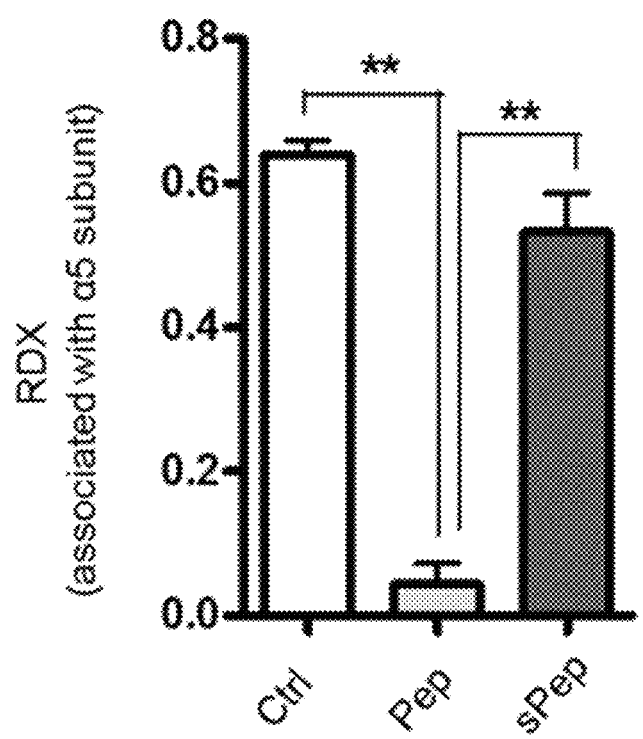

The data showed that the inhibitory peptide reduced the association between α5 subunit and radixin whereas the scramble peptide did not reduce this association (FIG. 2). These results show that the inhibitory peptide specifically disrupted the interaction of radixin with α5 subunit in vitro whereas the scramble peptide had no significant effect.

Example 2: Immunoprecipitation and Western Blotting Studies to Demonstrate Selectivity of Inhibitory Peptide In order to further demonstrate the specificity and selectivity of the inhibitory peptide, the immunoprecipitates from Example 1 were probed by WB using anti-gephyrin, anti-GABA$_A$ receptor α1 and α2 subunits (Santa Cruz Biotechnology) and anti β-actin (GenScript, Piscataway, NJ, USA) antibodies.

Figure 3A:
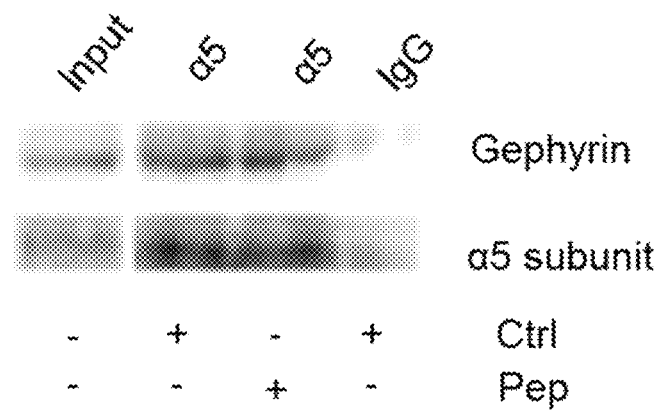
FIGS. 3A-3B depict the results of immunoprecipitation and Western Blot studies performed using anti-α5 and anti-gephyrin antibodies according to an embodiment of the present invention.
Figure 3B:
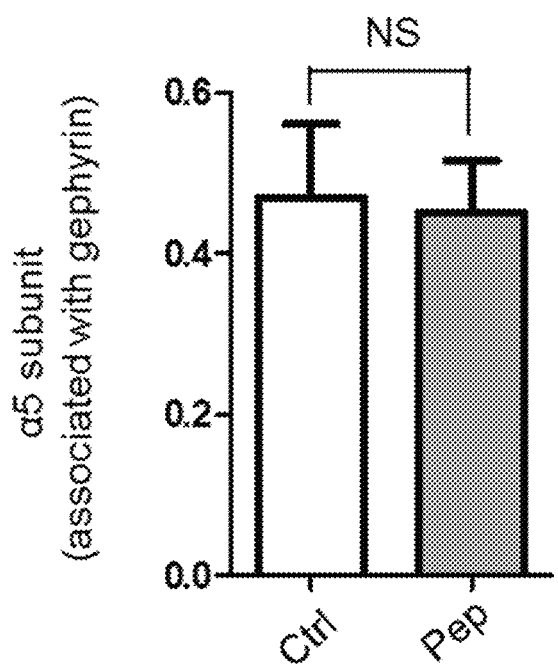
Figure 4A:
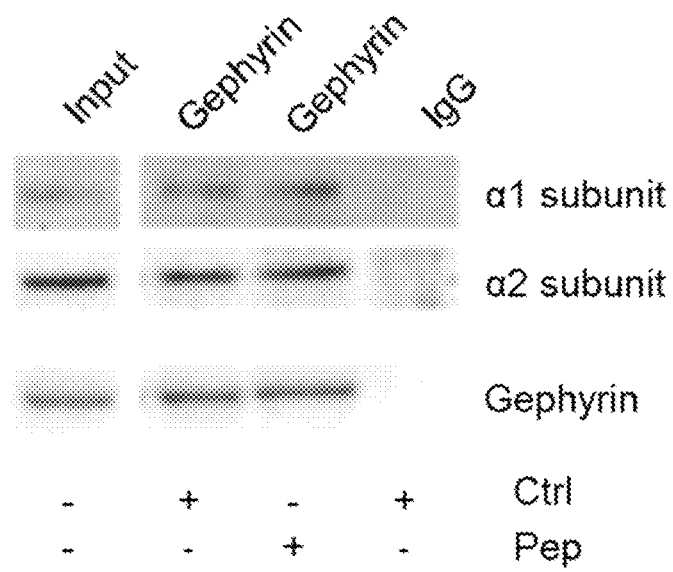
FIGS. 4A-4B depict the results of immunoprecipitation and Western Blot studies performed using anti-α1, anti-α2 and anti-gephyrin antibodies according to an embodiment of the present invention.
Figure 4B:
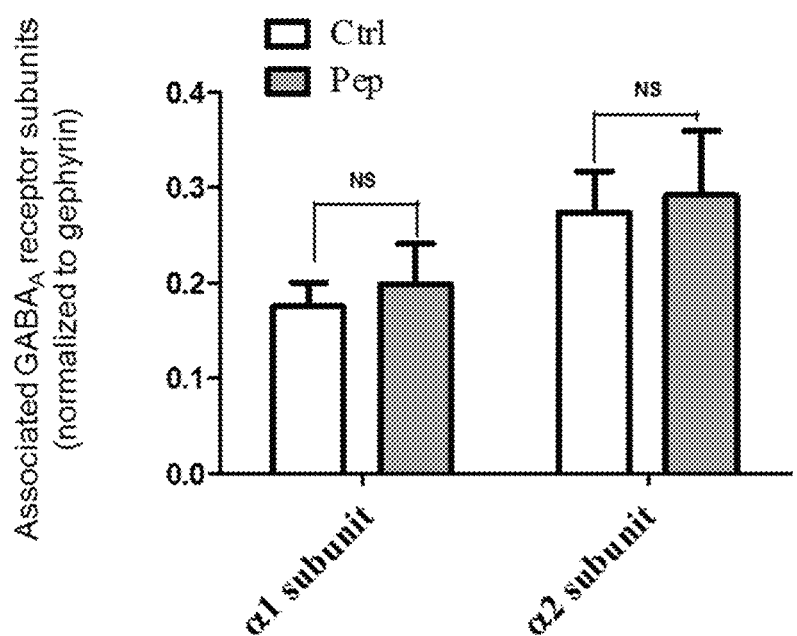

In the hippocampus, CA1 region in particular, α1 and α2 subunit containing GABA$_A$ receptors are highly expressed and are largely located at synaptic sites where they bind and interact with the scaffolding protein, gephyrin (Tyagaraj an, et al., 2014). This interaction with gephyrin regulates the synaptic plasticity. The α5 subunit, via the intracellular loop might also associate with gephyrin (Brady et al., 2015; Hausrat et al., 2015). Therefore, the ability of the inhibitory peptide to alter the interaction between gephyrin and GABA$_A$ receptor containing α1, α2 and α5 subunits was studied with Co-IP and WB assays. The immunoprecipitates from Example 1 were probed by WB using anti-gephyrin, anti-GABA$_A$ receptor α1, α2 and α5 subunit (Santa Cruz Biotechnology) antibodies The results showed that the inhibitory peptide did not interfere with gephyrin and α5 subunit interaction (FIG. 3), and did not have any effects on α1 and α2 subunit containing GABA$_A$ receptors in the hippocampal tissue (FIG. 4).

The results showed that the inhibitory peptide selectively and specifically targets the interaction between α5GABA$_A$ receptors and radixin.

Example 3: Modification of Inhibitory Peptide for Cell Transport

The inhibitory peptide was modified to incorporate a peptide to facilitate penetration of the cell membrane. Both the inhibitory peptide and the scramble peptide were fused to an 11-mer HIV-1 Tat sequence of protein transduction domain (Table 1), as described previously (Aarts et al., 2002; Fan et al., 2014).

Synthesis of the peptides was performed as described above.

TABLE 1

Peptide Sequences

| Peptide | Sequence* |
| --- | --- |
| α5 Inhibitory Peptide | NYFTKRGWAWDGKKAL (SEQ ID NO: 1) |
| α5 Scramble Peptide | TYFGRKNALWKAWKGD (SEQ ID NO: 5) |
| TAT - α5 Inhibitory Peptide | *YGRKKRRQRRR*NYFTKRGWAWDGKKAL (SEQ ID NO: 6) |
| TAT - α5 Scramble Peptide | *YGRKKRRQRRR*TYFGRKNALWKAWKGD (SEQ ID NO: 7) |

*The amino acids shown in italics are the TAT sequence

Example 4: Toxicity Study

The toxicity of the fused TAT-inhibitory peptides synthesized in Example 3 was studied by treating primary hippocampal neurons that were grown in dissociated cell culture with a serial concentration of the TAT-inhibitory peptide.

Primary Cell Cultures

Primary cultures of hippocampal neurons were prepared from Swiss White mice (Charles River, Montreal, Canada). Briefly, fetal pups (embryonic day 18) were removed from maternal mice that had been sacrificed by cervical dislocation. The hippocampi of each fetus were collected and placed on an ice-cooled culture dish. Neurons were then dissociated by mechanical trituration with a Pasteur pipette (tip diameter 150-200 μm) and plated on 35-mm culture dishes. The culture dishes were coated with collagen or poly-D-lysine (Sigma-Aldrich, Oakville, Canada). The density of neurons per culture dish was approximately 1×10⁶ cells. Two hours later, the medium was changed to a neurobasal medium supplemented with 2% B27 and 1% GlutaMAX (Life Technologies, Waltham, USA). The medium was changed every 3 days.

MTT Assay

After 24 hrs incubation with the fused peptides, cell survival was examined using the MTT assay, which measures the mitochondrial metabolism of 3-(4, 5-dimethylthiazol-2-yl)-2, 5-diphenyltetrazolium bromide (MTT) in the neurons.

Mitochondrial metabolism of 3-(4, 5-dimethylthiazol-2-yl)-2, 5-diphenyltetrazolium bromide (MTT) was used as an index of mitochondrial viability or cell viability. MTT solution was added to each well containing cultured hippocampal neurons at a final concentration of 5 µg/ml. The cells were incubated with MTT solution for 2 h at 37° C. Following the incubation, the medium containing MTT was removed, and 500 µl of DMSO was added to dissolve the intracellular purple formazan metabolite. The intensity of color was assessed using a microplate reader (Synergy-MX, BioTek Instrument Inc., Winooski, VT, USA) at a wavelength of 590 nm.

Figure 5:
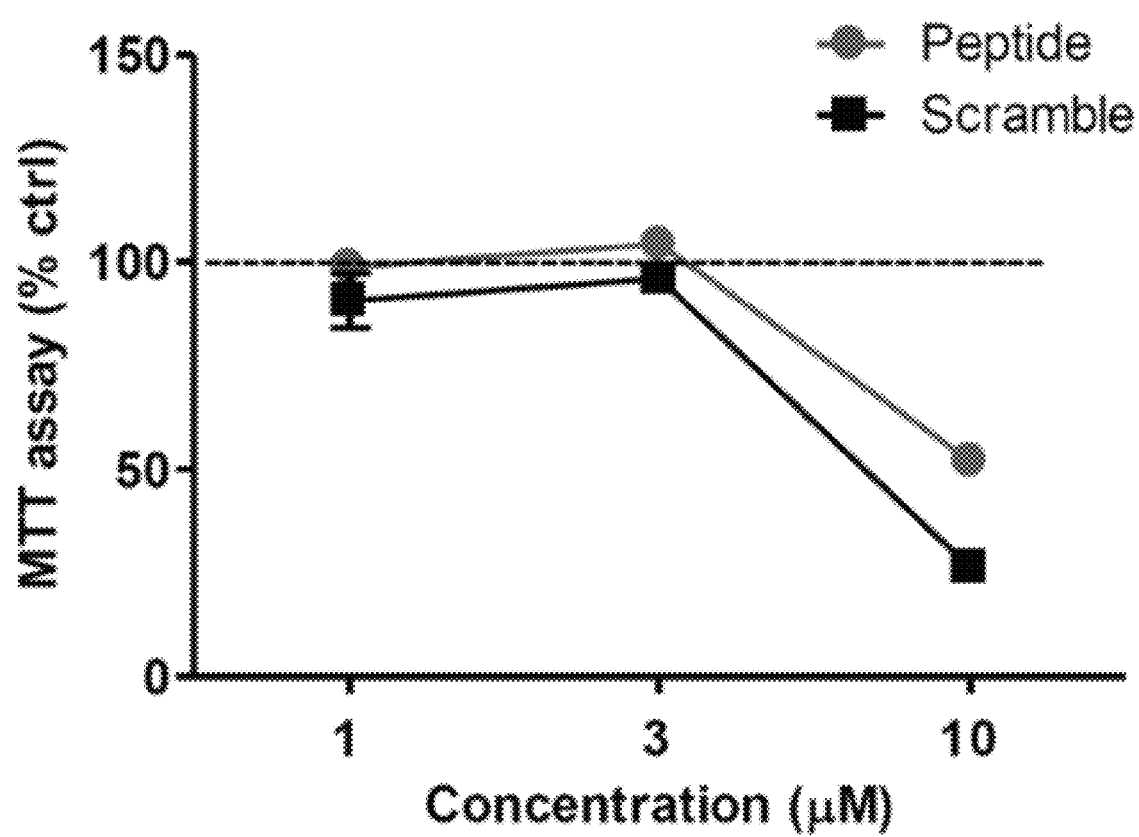
FIG. 5 depicts the results of the study of neurotoxicity of the inhibitory peptide in cultured hippocampal neurons according to an embodiment of the present invention.

The results of the MTT assay are shown in FIG. 5. Based on these in vitro studies, the peptides fused with TAT sequence are safe under the concentration of 3 µM for cultured hippocampal neurons. Furthermore, the toxicity levels observed from the inhibitory peptide and from the scramble peptides were similar, suggesting that the lack of toxicity that was observed was not sequence specific.

Example 5: Receptor Cell Surface ELISA Assay in Cell Culture Model

A culture model was developed which replicated the pathological increase in the number of α5GABA$_A$ receptors expressed on the surface of neurons as observed in various mood and cognitive disorders typically characterized or associated with memory and/or executive function loss.

This model was described in a recently published report that showed the general anesthetic, etomidate significantly augmented α5GABA$_A$ receptor cell-surface expression as evidenced by an increase in α5GABA$_A$ receptor-generated tonic conductance recorded 24 hrs after the treatment and an increase in protein levels in studies that used surface biotinylation and Western blotting. Noticeably, only neurons co-cultured with astrocytes or incubated with medium collected from astrocytes were able to produce the increase of tonic conductance (Zurek, et al., 2014).

This experimental cell culture model was used to test the effects of the inhibitory peptide on an overexpression of α5GABA$_A$ receptors on the surface of neurons. The medium from astrocytes that were treated with etomidate (1 µM, 1 hr) (conditioned medium) was collected, and the medium bathing cultured hippocampal neurons was exchanged with the astrocyte-conditioned medium. The cells were incubated at 37° C., 5% CO$_2$ with the peptide or scramble peptide (2 µM). After 24 hrs incubation, the cells were used for receptor cell-surface ELISA assay. The cells were fixed in 4% paraformaldehyde for 20 min in the presence (permeabilized) or absence (non-permeabilized) of 1% Triton-X100. The cells, after 3 times wash with cold PBS and blocked with 5% bovine album solution, were incubated with a α5 antibody (Santa Cruz Biotech Inc.) at 4° C. overnight. The next day the cells were thoroughly washed with PBS and incubated with the horseradish peroxidase (HRP)-conjugated secondary antibody for 2 hrs. With HRP substrate added and color developed in the medium, the results were determined with microplate reader.

Figure 6A:
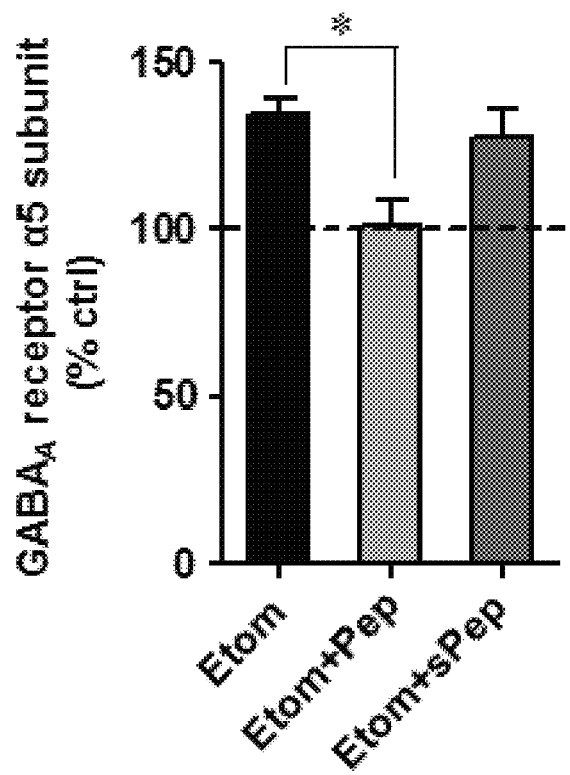
FIGS. 6A-6B depict the results of a study demonstrating the preventive effect of the inhibitory peptide on the etomidate-induced increase in GABA$_A$ receptor α5 subunit cell surface expression in neurons according to an embodiment of the present invention (Mean±SD, * P<0.05, ANOVA, n=3)

The cell surface expression of α5 subunit was presented as the ratio of the colorimetric reading under non-permeabilized conditions to those permeabilized conditions. Consistent with the previous report, etomidate increases α5GABA$_A$ receptor surface expression. This increase was blocked by the specific peptide, but not the scramble peptide (FIG. 6A). The results also verified that the peptide is membrane permeable.

Figure 6B:
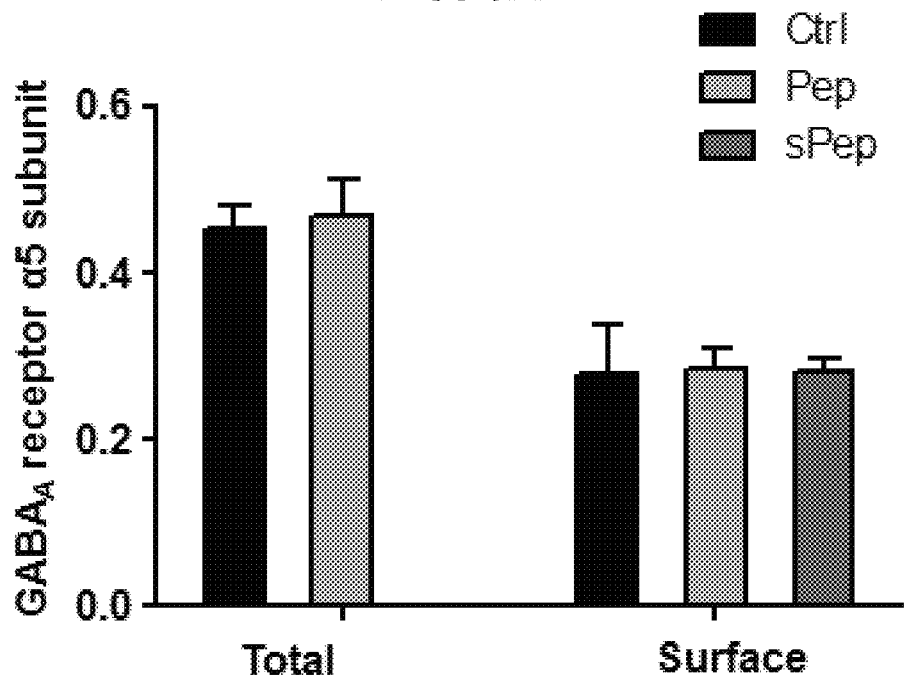

In addition, the effects of the inhibitory peptide on α5GABA$_A$ receptor expression or trafficking under basal conditions were studied. Similarly, neurons were treated with the peptide but without exposure to etomidate. The results showed the inhibitory peptide does not alter baseline of α5GABA$_A$ receptors expression either in total or the cell surface level under the non-pathological condition (FIG. 6B). These results showed that the peptide does not interfere with GABA$_A$ receptor normal function, which makes this inhibitor peptide (or other inhibitory agent, such as a peptidomimetic or related small molecule) particularly attractive as therapeutic agents, since it provides a benefit in pathological conditions without disturbing normal function.

For astrocyte culture, cortical astrocytes were isolated from embryonic day 18 (E18) mouse embryos. Cells were allowed to grow to confluence in MEM and 10% fetal bovine serum (FBS; Life Technologies, Grand Island, New York) for 14 d. Cells were then enzymatically dissociated with trypsin-EDTA (0.05%; Life Technologies, Grand Island, New York), and passaged three times to obtain a nearly pure astrocytic culture. Astrocytes were then plated at a density of 25,000 cells per dish.

Example 6: Inhibitory Peptides of Varying Length

The minimal amino acid sequence required for the inhibitory peptide to reduce α5GABA$_A$ receptor cell-surface expression was determined.

The peptide was truncated from either the N-terminus or C-terminus; the two truncated peptides were named α5pΔN4 and α5pΔC4, respectively (Table 2).

TABLE 2

Truncated Peptide Sequences

| Peptide | Sequence* |
|---|---|
| α5 Inhibitory Peptide | $^{342}$NYFTKRGWAWDGKKAL$^{357}$ (SEQ ID NO: 1) |
| α5pΔN4 | $^{346}$KRGWAWDGKKAL$^{357}$ (SEQ ID NO: 2) |
| α5pΔC4 | $^{342}$NYFTKRGWAWDG$^{353}$ (SEQ ID NO: 8) |

*The superscript numbers indicate the position of the peptide sequence within the amino acid sequence of the native α5 subunit.

Figure 7:
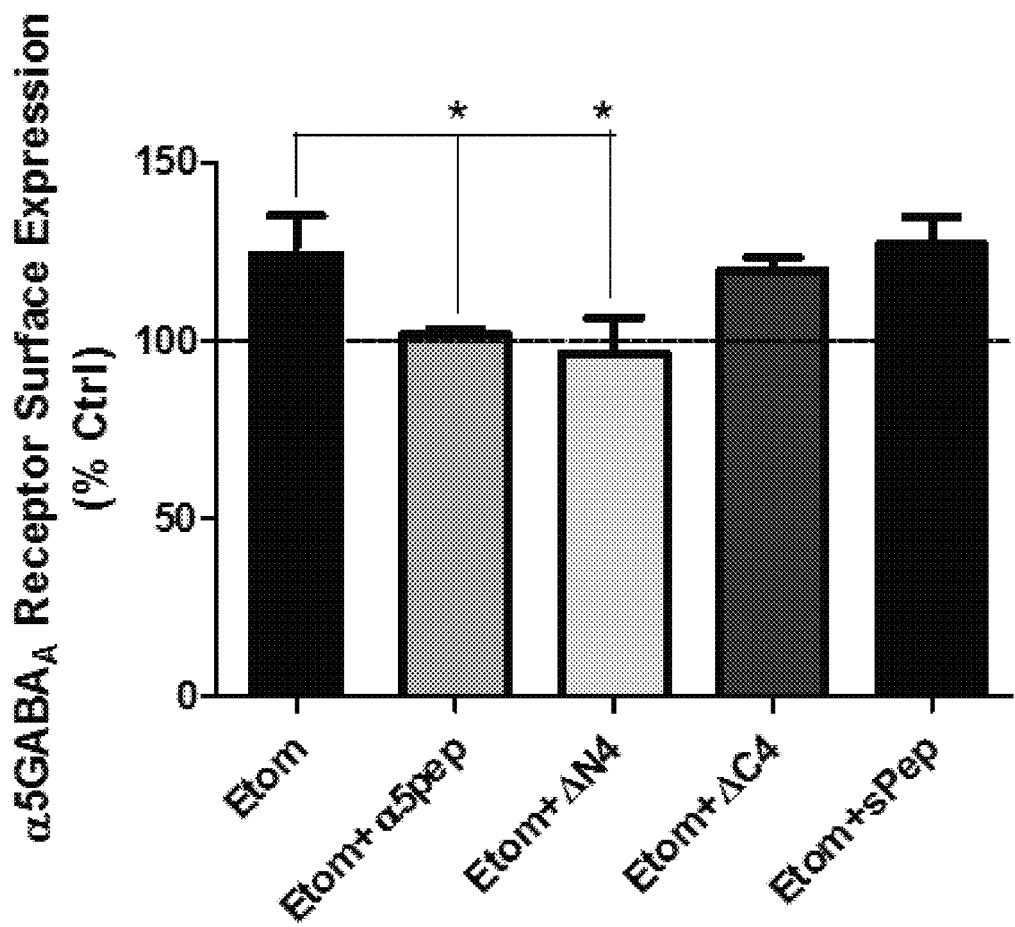
FIG. 7 graphically depicts the effect of truncation of the inhibitory peptide sequence on α5GABA$_A$ receptor surface expression according to an embodiment of the present invention (Mean±SD, P<0.05, n=3, ANOVA, one way)

An ELISA assay was performed in which hippocampal neurons were incubated with conditioned medium that contained α5 peptide and the N- and C-terminal truncated peptides (2 µM, each). After 24 hrs incubation, the cells were collected for α5 subunit cell surface expression analysis with ELISA assay. The neurons treated with the truncated peptides revealed that the α5pΔN4 (C-terminal portion maintained) peptide retains the inhibitory function, but α5pΔC4 (N-terminal portion maintained) lost the inhibitory function (FIG. 7). Based on this result, the α5pΔN4 peptide was further truncated from its N-terminus by deleting 2 amino acids cut-down each step (Table 3).

TABLE 3

N-terminal Truncated Peptides

| Peptide | Sequence* |
|---|---|
| α5pΔN4 | $^{346}$KRGWAWDGKKAL$^{357}$ (SEQ ID NO: 2) |
| α5p-C10 (c10) | $^{348}$GWAWDGKKAL$^{357}$ (SEQ ID NO: 3) |
| α5p-C8 (c8) | $^{350}$AWDGKKAL$^{357}$ (SEQ ID NO: 4) |
| α5p-C6 (c6) | $^{352}$DGKKAL$^{357}$ (SEQ ID NO: 9) |
| α5p-C4 (c4) | $^{354}$KKAL$^{357}$ (SEQ ID NO: 10) |

*The superscript numbers indicate the position of the peptide sequence within the amino acid sequence of the native α5 subunit.

Cultured neurons were incubated for 24 hrs with the conditional medium that contained each of the truncated peptides (2 µM). The expression of α5 subunit was analyzed with ELISA assay as described above.

Figure 8:
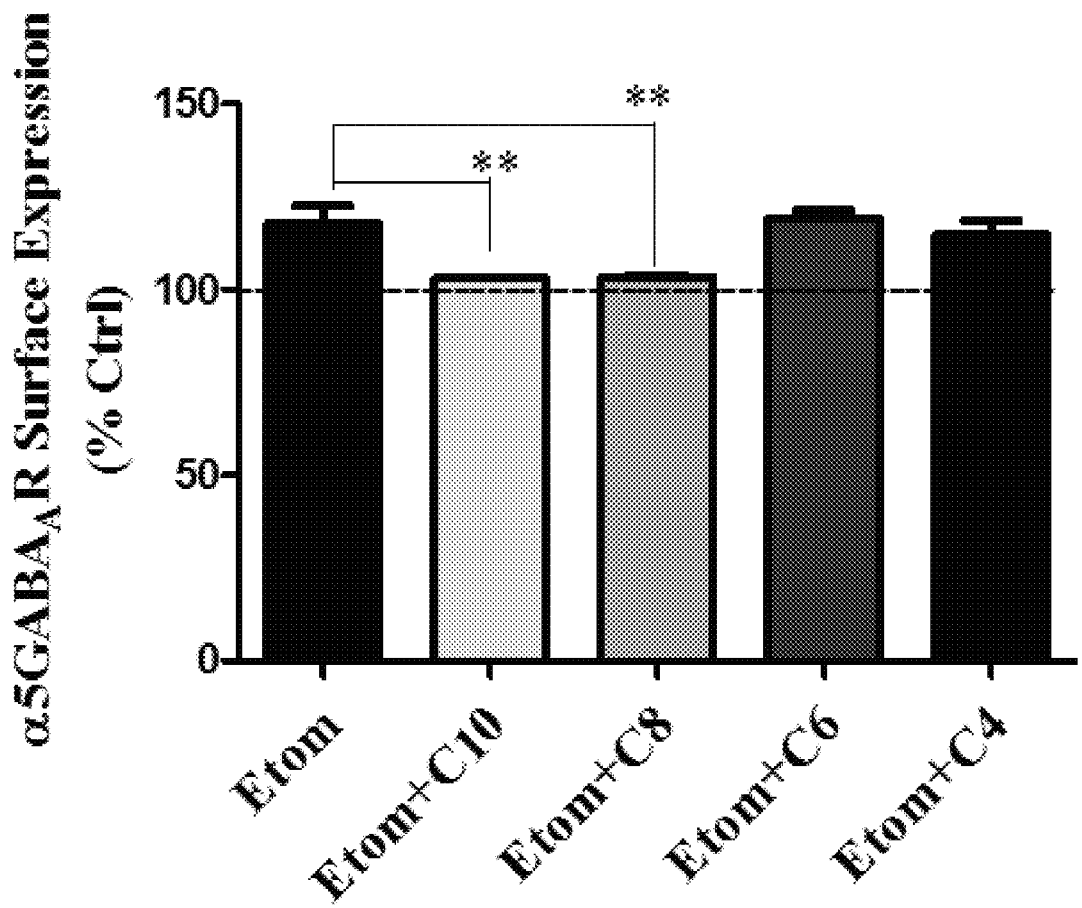
FIG. 8 graphically depicts the effect of the peptide length on the inhibition of α5GABA$_A$ receptor cell surface expression in cells treated with etomidate according to an embodiment of the present invention (Mean±SD, P<0.05, n=3, ANOVA, one way)
Figure 9A:
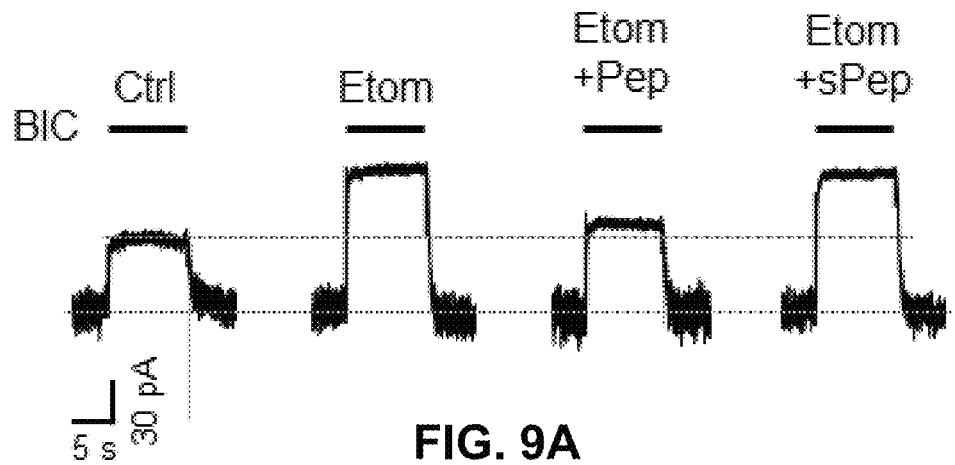
FIGS. 9A-9B depict the electrophysiological data showing the effect of the co-treatment with etomidate and the α5 peptide in hippocampal neurons when the α5 peptide is used to prevent etomidate-induced increase in tonic current according to an embodiment of the present invention.
Figure 9B:
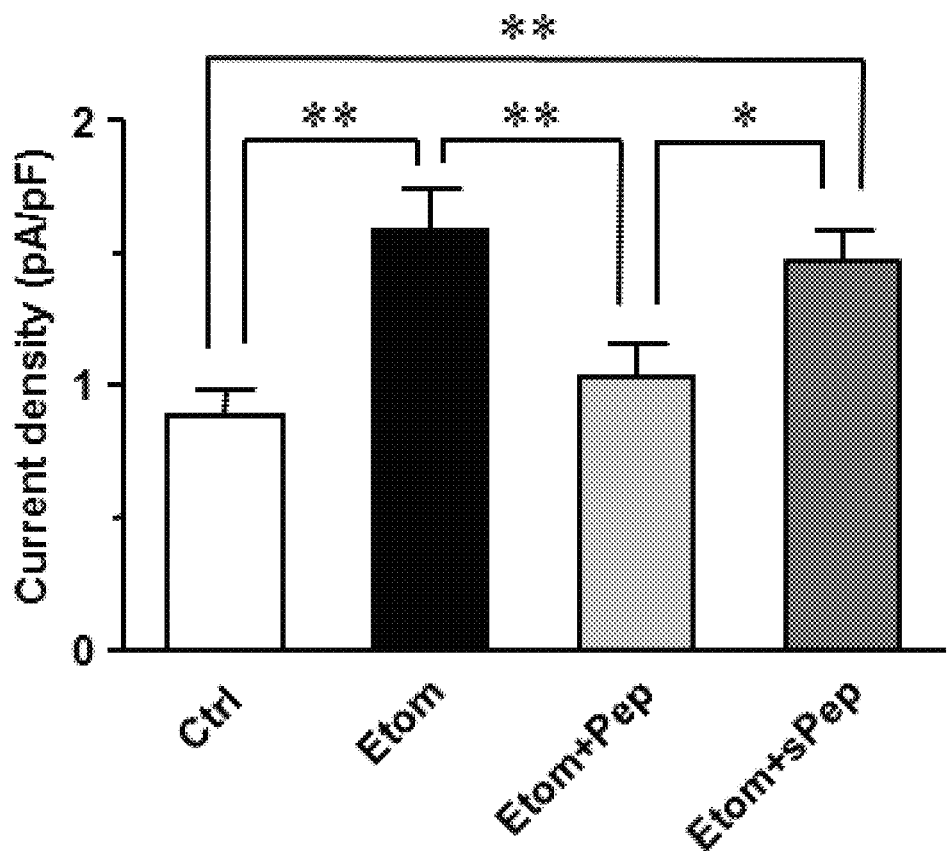

As shown in FIG. 8, the 8 amino acid sequence of the inhibitory peptide was necessary or the minimal required for the peptide to block α5GABA$_A$ receptor trafficking and cell surface expression. However, as would be appreciated by those of skill in the art, conservative variants of this peptide will have a similar inhibitory activity. C10 and C8 peptides prevented the etomidate-induced α5GABA$_A$ receptor surface expression, but C6 and C4 peptides did not Example 7: Whole-Cell Voltage-Clamp Recordings If the peptide reduces α5GABA$_A$ receptors on the cell surface expression, it may be anticipated that it may reduce the GABA$_A$ receptor mediated tonic current in hippocampal neurons. FIGS. 9A and 9B show the results of testing the effects of inhibitory peptide on the amplitude of the GABA$_A$ receptor-mediated tonic current in neurons grown in astrocyte-neuronal cell co-cultures. Note that the sustained increase in GABA$_A$ receptor mediated-tonic current that is triggered by general anesthetics occurs only when neurons are grown in co-culture with astrocytes, but not when neurons are cultured alone. The hippocampal neurons that were co-cultured with cortical astrocytes were treated with etomidate, vehicle, etomidate plus inhibitory peptide, or etomidate plus the scramble peptide. The tonic current was measured using standard whole cell recording methods. The results showed that etomidate caused an increase in the amplitude of the tonic current, measured 24 h after the drug treatment. Co-treatment with inhibitory peptide, but not the scramble peptide, reversed the increase in tonic current.

For astrocyte-neuron coculture, astrocyte cell suspension was placed over hippocampal neurons cultured at 7 d in neurobasal media. Astrocytes were monitored visually to ensure survival and confluence for the duration of the experiment. The neurons were maintained in culture for 14-20 days before use. At this point in time, hippocampal neurons become appropriately polarized, develop extensive axonal and dendritic arbors and form numerous, functional synaptic connections with one another, which resemble mature hippocampal neurons in vivo. Culture dishes were prepared from at least two different mice for each experiment, and a maximum of two cells were recorded from each dish.

Whole-cell currents were recorded under voltage-clamp (−60 mV) conditions using an Axopatch 200A amplifier (Molecular Devices, Sunnyvale, CA, USA) controlled with pClamp 9.0 software (Molecular Devices) via a Digidata 1322 interface (Molecular Devices). Patch pipettes with open-tip resistances of 2-3 MΩ were pulled from thin-walled borosilicate glass capillary tubes. Extracellular recording solution contained (in mM): 140 NaCl, 2 CaCl$_2$, 1 MgCl$_2$, 5.4 KCl, 25 N-2-hydroxy-ethylpiperazine-N'-2-ethanesulphonic acid (HEPES), 28 glucose (pH 7.4, 320-330 mOsm). Intracellular solution contained (in mM): 140 CsCl, 10 HEPES, 11 EGTA, 4 MgATP, 2 MgCl$_2$, 1 CaCl$_2$), 2 TEA and 4 MgATP (pH 7.3 with CsOH, 285-295 mOsm). A computer-controlled, multibarrelled perfusion system (SF-77B, Warner Instruments, Hamden, USA) was used to apply the extracellular solution to neurons. 6-Cyano-7-nitroquinoxaline-2,3-dione (CNQX, 10 µM) and (2R)-amino-5-phosphonovaleric acid (APV, 20 µM) were added to the extracellular solution to block ionotropic glutamate receptors. Tetrodotoxin (0.2 µM) was also added to the extracellular solution to block voltage-dependent sodium channels.

Etomidate (1 µM) or vehicle solution was used to treat the culture dish for 1 h. The media was then removed and replaced with fresh culture media. For some etomidate-treated dishes, the inhibitory peptide or scramble peptide was co-treated with etomidate for 1 h. The media was then removed and replaced with fresh culture media containing the peptide or the scramble peptide. Recordings were performed 24 h later. To measure the amplitude of the tonic current, exogenous GABA (0.5 µM) was added to the extracellular solution and the change in holding current was measured during application of bicuculline (20 µM). GABA (0.5 µM) is similar to physiological levels of extracellular GABA that occur in vivo.

Example 8: Reduction of α5GABA$_A$ Receptor Expression

Figure 10A:
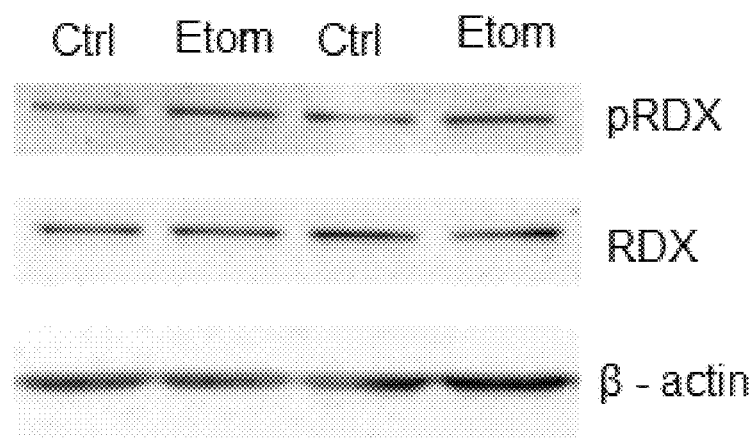
FIGS. 10A-10C depict the results of studies to demonstrate radixin phosphorylation and total protein expression in mouse model treated with saline or etomidate according to an embodiment of the present invention.
Figure 10B:
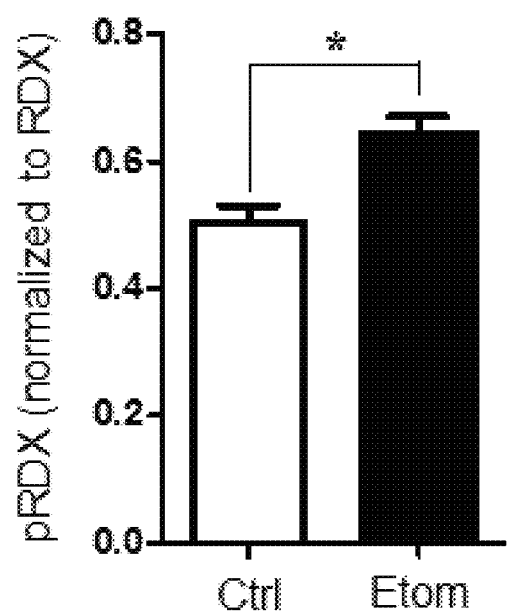
Figure 10C:
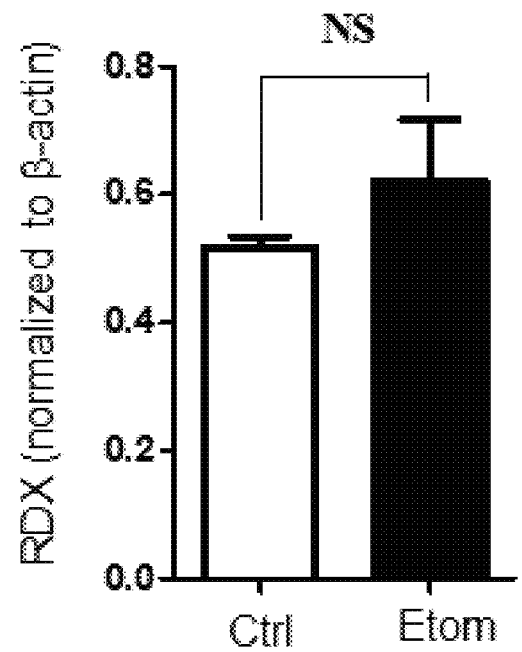
Figure 11A:
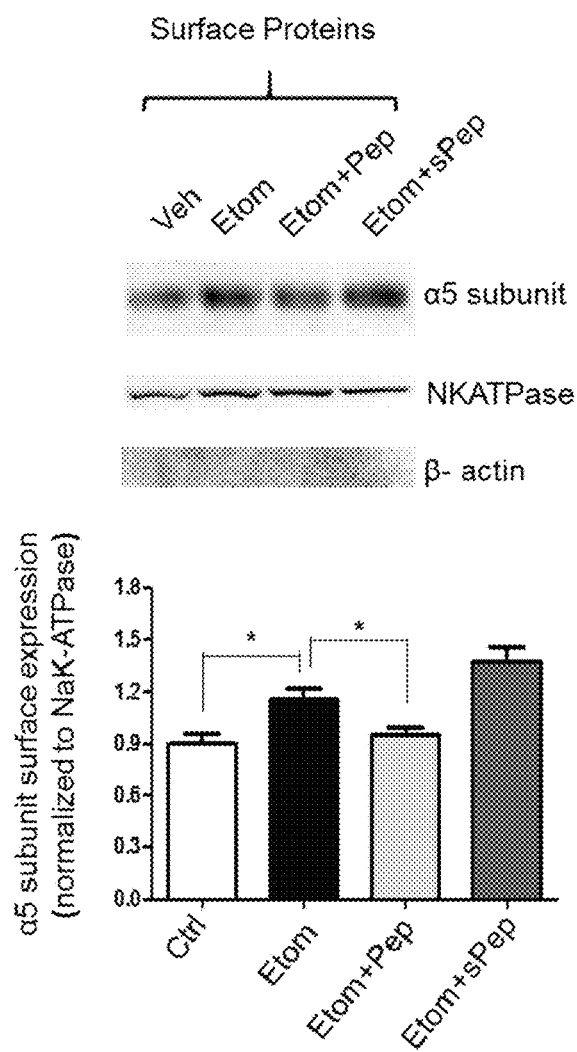
FIGS. 11A-11B depict the effects of the peptide and scramble peptide on the etomidate-induced α5 subunit surface expression ex vivo according to an embodiment of the present invention.
Figure 11B:
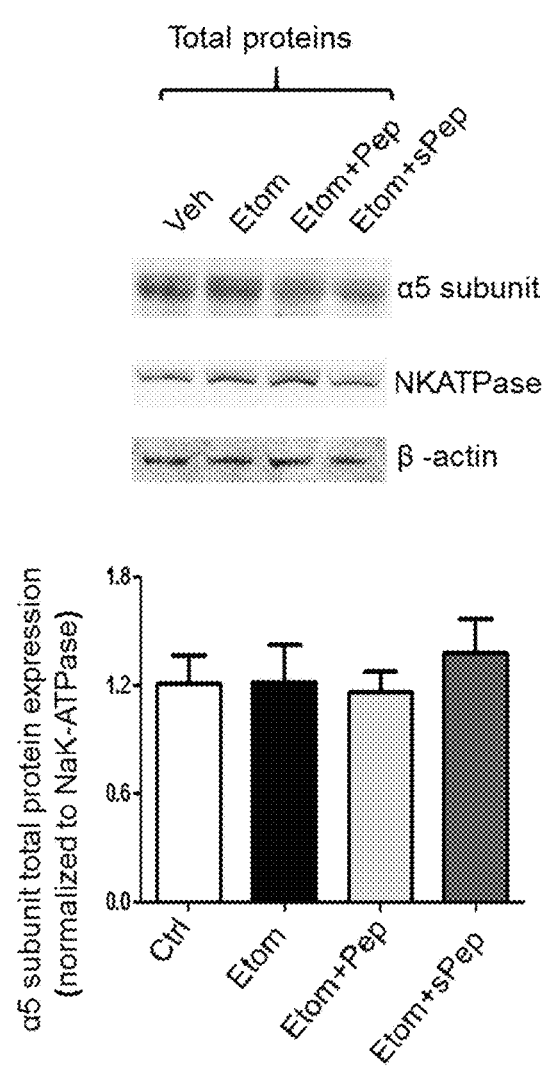

We next asked whether injection of inhibitory peptide, when administered to mice in vivo by I.P. injection, reduced the level of α5GABA$_A$ receptors expressed in the hippocampus. To test whether the peptide reduces α5GABA$_A$ receptor cell-surface expression in vivo, we took advantage of a mouse model that we developed recently (Zurek, et al., 2014), in which up-regulation of α5GABA$_A$ receptor cell surface expression causes memory deficits. Adult mice (22-25 g) were treated with etomidate (8 mg/kg, i.p.), and sacrificed 24 hrs later according to a protocol approved by the Animal Care Committee of the University of Toronto. The hippocampi were collected and subject to experiments. We first measured the level of radixin phosphorylation, because radixin phosphorylation is required for the recruitment of α5GABA$_A$ receptors to extrasynaptic sites of the neurons (Loebrich et al., 2006; Hausrat et al., 2015). The antibody against threonine at 564 of radixin, which is specific for radixin phosphorylation involving α5GABA$_A$ receptor extra-synaptic trafficking, was used for these studies (Choii et al., 2015; Hausrat et al., 2015). The results showed that treatment with etomidate increases radixin phosphorylation but does not alter total radixin protein level (FIG. 10), suggesting that etomidate increases α5GABA$_A$ receptor cell surface expression via enhancing radixin phosphorylation. We next examined whether the inhibitory peptide prevented α5GABA$_A$ receptor from trafficking to surface membrane in vivo by studying ex vivo brain slices. We administrated the peptide or scramble peptide (20 mg/kg, i.p.) to adult mice (male) then examined α5 subunit on cell surface expression using the surface biotinylation assay, which specifically labeled proteins expressed on the cell surface. The results showed that the peptide selectively prevented the expression of α5GABA$_A$ receptors on the cell surface expression (FIG. 11A), but did not change α5GABA$_A$ total protein production (FIG. 11B).

Example 9: Novel Object Recognition Task—Use of Peptide to Prevent Memory Impairment The NOR task is a widely used model for investigation into memory alterations (Antunes and Biala 2012). This test is sensitive enough to detect alteration in animal behavior, and has been employed to evaluate the influence of clinically used drugs in animals' memory and recognition. For example, animals that were exposed to cocaine in prenatal period displayed a preference for the novel object when tested later (Schindler et al. 2010). Another psychostimulant drug, methamphetamine decreased the novelty index significantly in adult rats (Herring et al. 2008), and can produce a profound, persistent, and selective deficit for both short- and long-term retention in the NOR task (Schroder et al 2003). Other drugs, such as lidocaine (Hammond et al 2004), ketamine (Goulart et al. 2010), caffeine (Botton et al. 2010), neuroactive steroids (Nanfaro et al. 2010), and hormones (Walf et al. 2009 and Aubele et al. 2008) can also alter NOR task which are consistent with the effects of these drugs on learning and memory in humans. In summary, the NOR task is a validated tool to test the pharmacological effects of a drug, to understand the cognitive profile of a clinical disorder with the aim of developing a targeted therapeutic (Antunes and Biala 2012).

Furthermore, α5GABA$_A$ receptors are expressed in high levels in the hippocampus where they effectively disrupt some forms of memory performance. For example, it has been previously shown that an increase in receptor function impairs performance in the novel object recognition task ("NOR", Zurek et al., 2014 JCI). Therefore, the NOR task was selected to determine whether the exemplary inhibitory peptide altered cognitive performance in terms of both preventing and treating memory deficit. The NOR task is a well-validated and widely used behavioral assay that is used to study declarative and recognition memory in laboratory animals and humans. For example, drugs such as caffeine, ampakines, nicotine, which were found to improve performance using the NOR test in rodents, are known to also improve cognition in humans (Costa et al. 2008 and Borota et al. 2014, Damgaard et al. 2010, Ingvar et al. 1997, Tian et al. 2015, Heishman et al. 2010). These studies show that the NOR studies in animals may be used to predict the utility of the drug for changing human cognitive behaviors. Here, we showed the inhibitory peptide both prevented and treated (reversed) memory deficits triggered by a previous exposure to the general anesthetic etomidate.

The novel object recognition task involves the presentation of two identical objects for visual inspection (in the case of humans and non-human primates) and exploration in the case of rodents. After a delay, one of the original objects is presented together with a new (novel) object. Humans and animals normally spend time more time looking at (or in the case of mice, exploring) the novel object. Indeed, the test relies on the innate preference of humans and animals for novelty. The inspection or interaction time differs only if the familiar object is recognized. Otherwise, the subject spends an equal amount of time inspecting both objects. Time spent observing (or interacting) the novel object and the familiar object is used as a surrogate measure of the memory for the familiar object. Scores are high if the previously presented (familiar) object is recognized and more time was spent with the novel object whereas scores are low if there is no recall and interaction times resulted from random chance encounters with the both objects.

In the present study, mice were handled two times a day, 5 min each before start of behavioral experiments. Object recognition was assessed in a circle opaque chamber with the diameter of 38.5 cm in a regular lit room. Each mouse was habituated to the chamber for 5 min since day 3. During the training phase, the mouse was allowed to explore two identical objects for 5 min. The mouse was then returned to its home cage for a retention period of 1 h. The mouse was reintroduced to the training context and presented with one familiar object and one novel object for 5 min. Movement and interaction with the objects was recorded with a video camera that was mounted above the chamber. The exploratory behavior and mouse activity was analyzed blindly by a person with a good training and the software EthoVision, XT v11.5 provided by the Noldus Information Tech Inc., (Leesburg VA, USA). Exploratory behavior was defined as sniffing, licking, or touching the object while facing the object. Memory was assessed by measuring the novelty preference ratio (i.e., the ratio of time spent exploring the novel object to the time spent exploring both objects). Mice that exhibited a preference ratio greater than the value of chance (0.5) were deemed to have remembered the familiar object. Animals that did not interact for a minimum of 1 s with each object during the test period were excluded. Total interaction time with both objects was compared between groups to determine whether the treatments affected locomotor activity or exploration during the testing phase.

Figure 12:
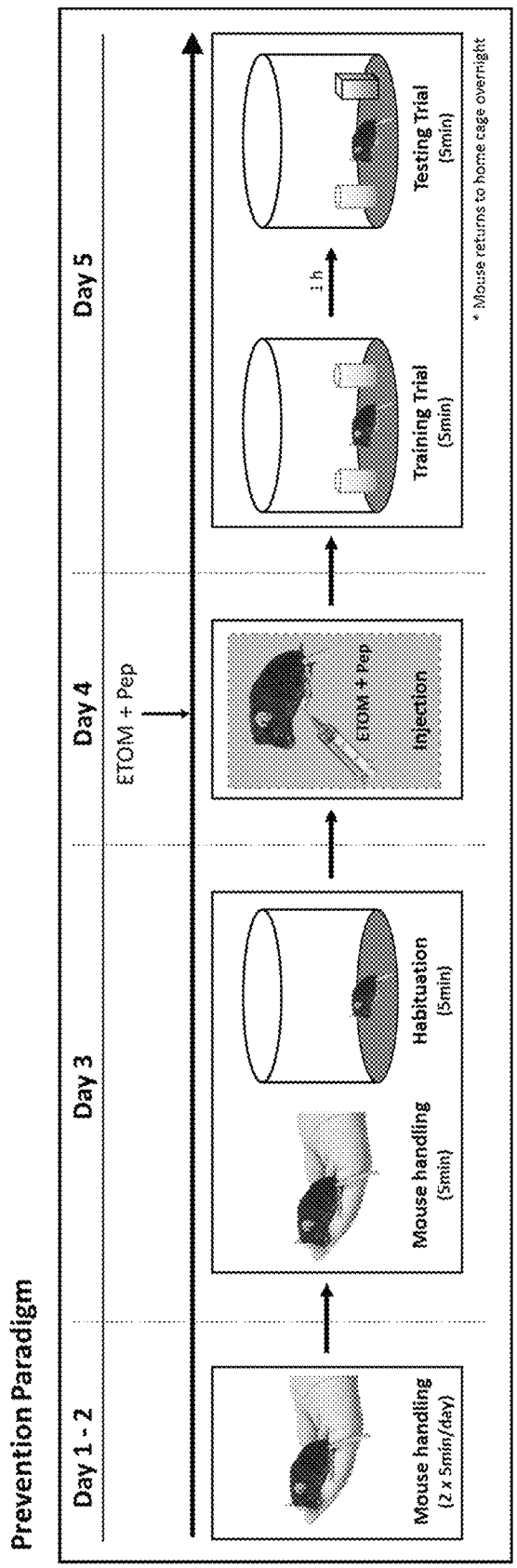
FIG. 12 shows a schematic illustration of the timeline experimentation for the prevention paradigm according to an embodiment of the present invention.
Figure 13:
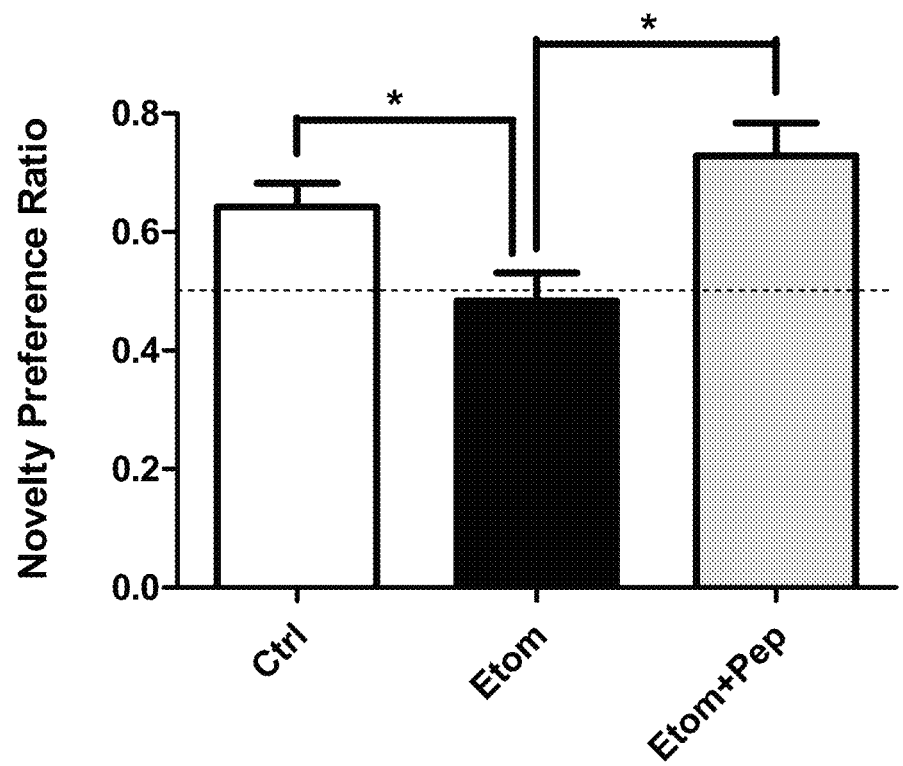
FIG. 13 provides data for the preventive effect of the α5 peptide on the memory impairment caused by the general anesthetic etomidate according to an embodiment of the present invention (data shown as mean±SEM, * P<0.05, one-way ANOVA and Tukey's multiple comparison test, 4-9 mice per group)

Specifically, we studied whether the use of the inhibitory peptide with etomidate prevented etomidate-induced memory deficits (attributed to the increase in cell surface expression of α5GABA$_A$ receptors). As shown in FIG. 12, the mice (2 months old, male) were treated (i.p.) with Etom (8 mg/kg), or Etom plus α5 peptide (20 mg/kg). Saline and 35% propylene glycol were used as the vehicle control. NOR was conducted the next day. The results shows that the peptide could prevent the etomidate-induced memory deficits (FIG. 13). The etomidate-treated mice showed no preference for the novel object whereas the etomidate-treated mice who also received the peptide showed preference for the novel object. This difference was not due to the effect of the peptide on locomotion or general behavior of the mice, as the peptide did not impair the ability to move (Table 4) and the body state (Table 5) of the mice.

TABLE 4

Mouse Movement comparison

| Treatment | Total Distance (CM) | Velocity (cm/s) | | |
|---|---|---|---|---|
| | | Minimum | Maximum | Mean |
| Veh | 1599 ± 236 | 0.0042 ± 0.002 | 43.8 ± 7.7 | 5.3 ± 0.8 |
| +Pep | 1402 ± 100 | 0.0040 ± 0.003 | 39.5 ± 4.9 | 4.7 ± 0.3 |
| P value | 0.165 | 0.165 | 0.925 | 0.355 |

TABLE 5

Mice remained healthy during the studies as evidenced by the Mouse Body State Comparison

| Treatment | Body Elongation State (s) | | Body Angle State (s) | | Rotation |
|---|---|---|---|---|---|
| | Stretched | Normal (%) | Contracted (%) | Straight (%) | Bent (%) | Frequency |
| Veh | 0 | 236 ± 55 (79%) | 64 ± 55 (21%) | 258 ± 47 (96%) | 10 ± 5 (4%) | 4.8 ± 1.9 |
| +Pep | 0 | 252 ± 66 (84%) | 48 ± 66 (16%) | 269 ± 45 (98%) | 6 ± 3 (2%) | 5.5 ± 1.7 |
| P (Veh vs + Pep) | | P > 0.05 | P > 0.05 | P > 0.05 | P > 0.05 | P > 0.05 |

Figure 14:
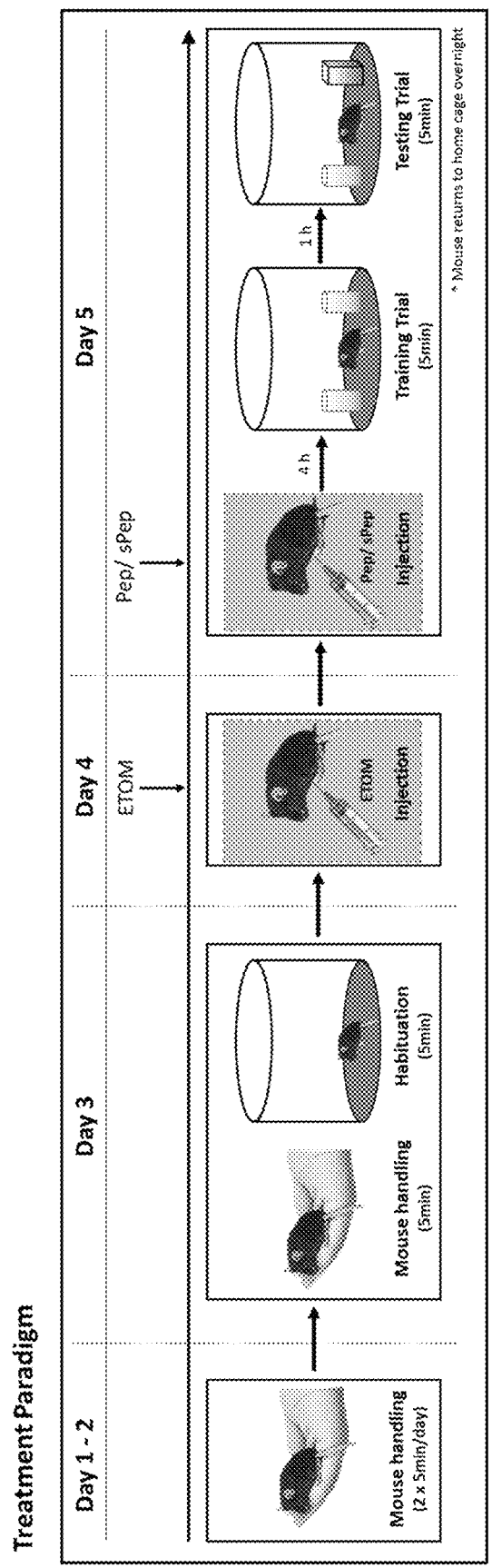
FIG. 14 shows a schematic illustration of the timeline experimentation for the treatment paradigm according to an embodiment of the present invention.
Figure 15:
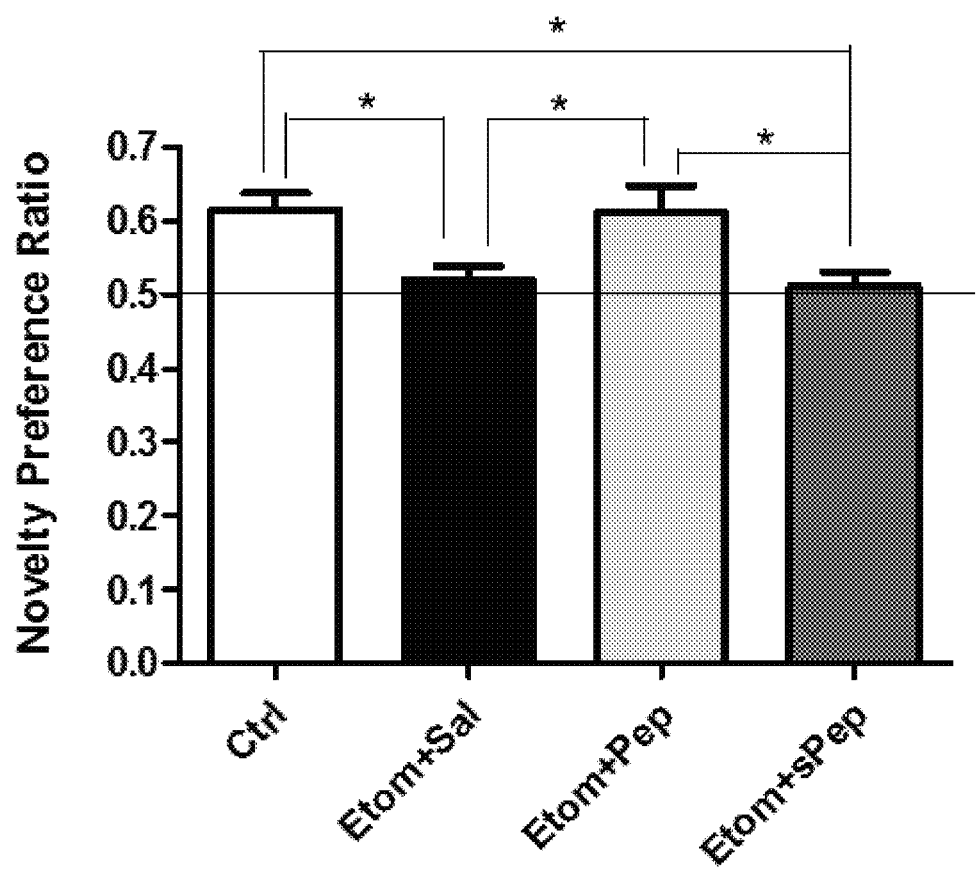
FIG. 15 provides data for the treatment effect of the α5 peptide on the memory impairment caused by the general anesthetic etomidate according to an embodiment of the present invention (data shown as mean±SEM, 4 mice per group)
Figure 16A:
FIGS. 16A-16C depict the persistent increase of tonic current caused by inhaled anesthetics (isoflurane, sevoflurane), benzodiazepines (midazolam), and propofol according to an embodiment of the present invention ((FIG. 16A) midazolam (MDZ, 200 nM)
Figure 16A:
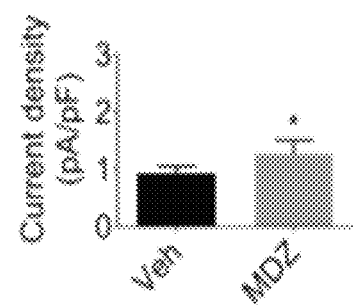
Figure 16B:
Figure 16B:
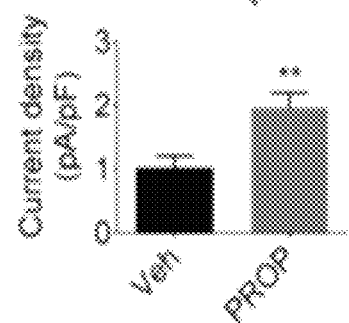
Figure 16C:
Figure 16C:
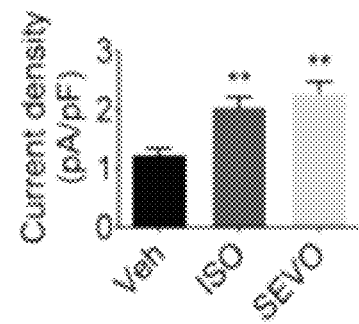

Example 10: Novel Object Recognition Task—Use of Peptide to Treat Memory Impairment We next tested whether the peptide was effective at reversing memory deficits as they were established. As described above and in previous studies, treatment with etomidate induces memory deficits. Control mice received no etomidate. We studied whether treating mice that had etomidate-induced memory deficits with the peptide restored memory performance. The experimental protocol is shown in FIG. 14. Adult male mice were first treated with etomidate (to induce memory loss). The following day, subgroups of mice were treated with the inhibitory peptide, saline or the scramble peptide 4 hrs before behavioral testing, using the NOR test as described in Example 9. The inhibitory peptide but not the scramble peptide reversed the memory deficits in etomidate-treated mice (FIG. 15). The Etom+Sal group showed no preference for the novel object. Similarly, the group who received the scramble peptide also showed no preference for the novel object. However, the group who received the peptide showed preference for the novel object.

Statistical Analyses

Results are presented as mean±SEM. Significance was determined using a Student's t-test or ANOVA with post hoc tests to determine differences among more than two groups. Differences were considered significant at P<0.05.

REFERENCES

Aarts, M., et al., Treatment of ischemic brain damage by perturbing NMDA receptor-PSD-95 protein interactions. Science, 2002. 298(5594): p. 846-50.

Asai, Y., et al. (2008) GABAA/Benzodiazepine receptor binding in patients with schizophrenia using [11C]Ro15-4513, a radioligand with relatively high affinity for alpha5 subunit. Schizophrenia research 99:333-40.

Atack, J. R., et al., In vivo labelling of alpha5 subunit-containing GABA(A) receptors using the selective radioligand [(3)H]L-655,708. Neuropharmacology, 2005. 49(2): p. 220-9.

Atack, J. R., Preclinical and clinical pharmacology of the GABAA receptor alpha5 subtype-selective inverse agonist alpha5IA. Pharmacol Ther, 2010. 125(1): p. 11-26.

Bechara, C. & Sagan, S. "Cell penetrating peptides: 20 years later, where do we stand?" FEBS Letters (2013) 587 (12) 1693-1702.

Botta, P., et al. (2015) Regulating anxiety with extrasynaptic inhibition. Nature neuroscience 18:1493-500.

Brady, M. L., and T. C. Jacob, Synaptic localization of alpha5 GABA (A) receptors via gephyrin interaction regulates dendritic outgrowth and spine maturation. Dev Neurobiol, 2015. 75(11): p. 1241-51.

Braudeau, J., B. et al. (2011) Specific targeting of the GABA-A receptor alpha5 subtype by a selective inverse agonist restores cognitive deficits in Down syndrome mice. J Psychopharmacol 25:1030-42.

Caraiscos, V. B., et al., Tonic inhibition in mouse hippocampal CA1 pyramidal neurons is mediated by alpha5 subunit-containing gamma-aminobutyric acid type A receptors. Proc Natl Acad Sci USA, 2004a. 101:3662-3667.

Choii, G. and J. Ko, (2015) Exp Mol Med, 47: p. e158 entitled Gephyrin: a central GABAergic synapse organizer.

Clarkson, A. N., et al. (2010) Reducing excessive GABA-mediated tonic inhibition promotes functional recovery after stroke. Nature 468:305-9.

Craddock, N. and M. J. Owen (2005) The beginning of the end for the Kraepelinian dichotomy. The British journal of psychiatry: the journal of mental science 186:364-6.

Crestani, F., et al., Trace fear conditioning involves hippocampal alpha5 GABA(A) receptors. Proc Natl Acad Sci USA, 2002. 99(13): p. 8980-5.

Fan, X., et al., Rapid and reversible knockdown of endogenous proteins by peptide-directed lysosomal degradation. Nat Neurosci, 2014. 17(3): p. 471-80.

Fatemi, S. H., et al. (2010) mRNA and protein levels for GABAAalpha4, alpha5, beta1 and GABABR1 receptors are altered in brains from subjects with autism. Journal of autism and developmental disorders 40:743-50.

Fischell, J., et al. (2015) Rapid Antidepressant Action and Restoration of Excitatory Synaptic Strength After Chronic Stress by Negative Modulators of Alpha5-Containing GABAA Receptors. Neuropsychopharmacology: official publication of the American College of Neuropsychopharmacology 40:2499-509.

Gill, K. M., et al. (2011) A novel alpha5GABA(A)R-positive allosteric modulator reverses hyperactivation of the dopamine system in the MAM model of schizophrenia. Neuropsychopharmacology: official publication of the American College of Neuropsychopharmacology 36:1903-11.

Hausrat, T. J., et al., Radixin regulates synaptic GABAA receptor density and is essential for reversal learning and short-term memory. Nat Commun, 2015. 6: p. 6872.

Jo, S., O. et al. (2014) GABA from reactive astrocytes impairs memory in mouse models of Alzheimer's disease. Nature medicine 20:886-96.

Leite, D. M., et al., Peptide Self-Assemblies for Drug Delivery. Curr Top Med Chem, 2015. 15(22): p. 2277-89.

Loebrich, S., et al., Activated radixin is essential for GABAA receptor alpha5 subunit anchoring at the actin cytoskeleton. EMBO J, 2006. 25(5): p. 987-99.

Luscher, B. and C. A. Keller, Regulation of GABAA receptor trafficking, channel activity, and functional plasticity of inhibitory synapses. Pharmacol Ther, 2004. 102(3): p. 195-221.

Macchi, S. et al. (November 2015) "Spontaneous membrane-translocating peptides: influence of peptide self-aggregation and cargo polarity." Science Reports 16; 5; 16914.

Martin L. J., et al. (2010) J Neurosci., 30(15):5269-82 entitled Alpha5GABAA receptor activity sets the threshold for long-term potentiation and constrains hippocampus-dependent memory.

Martinez-Cue, C., et al. (2014) Treating enhanced GABAergic inhibition in Down syndrome: use of GABA alpha5-selective inverse agonists. Neuroscience and biobehavioral reviews 46 Pt 2:218-27.

Mendez, M. A., et al. (2013) The brain GABA-benzodiazepine receptor alpha-5 subtype in autism spectrum disorder: a pilot [(11)C]Ro15-4513 positron emission tomography study. Neuropharmacology 68:195-201.

Mohler, H. (2012) Cognitive enhancement by pharmacological and behavioral interventions: the murine Down syndrome model. Biochemical pharmacology 84:994-9.

Nutt, D., GABAA receptors: subtypes, regional distribution, and function. J Clin Sleep Med, 2006. 2(2): p. S7-11.

Nutt, D. J., et al., Blockade of alcohol's amnestic activity in humans by an alpha5 subtype benzodiazepine receptor inverse agonist. Neuropharmacology, 2007. 53(7): p. 810-20.

Olsen, R. W. and W. Sieghart, International Union of Pharmacology. LXX. Subtypes of gamma-aminobutyric acid (A) receptors: classification on the basis of subunit composition, pharmacology, and function. Update. Pharmacol Rev, 2008. 60(3): p. 243-60.

Papadimitriou, G. N., et al. (1998) Association between the GABA(A) receptor alpha5 subunit gene locus (GABRA5) and bipolar affective disorder. American journal of medical genetics 81:73-80.

Papadimitriou, G., et al. (2001) Association between GABA-A receptor alpha 5 subunit gene locus and schizophrenia of a later age of onset. Neuropsychobiology 43:141-4.

Pettingill, P., et al., Antibodies to GABAA receptor alpha1 and gamma2 subunits: clinical and serologic characterization. Neurology, 2015. 84(12): p. 1233-41.

Potier, M. C., et al. (2014) Reducing GABAergic inhibition restores cognitive functions in a mouse model of Down syndrome. CNS & neurological disorders drug targets 13:8-15.

Prut, L., et al., A reduction in hippocampal GABAA receptor alpha5 subunits disrupts the memory for location of objects in mice. Genes Brain Behav, 2010. 9(5): p. 478-88.

Rudolph, U. and H. Mohler, GABAA receptor subtypes: Therapeutic potential in Down syndrome, affective disorders, schizophrenia, and autism. Annu Rev Pharmacol Toxicol, 2014. 54: p. 483-507.

Saab, B. J., et al. (2010) Short-term memory impairment after isoflurane in mice is prevented by the alpha5 gamma-aminobutyric acid type A receptor inverse agonist L-655,708. Anesthesiology 113:1061-71.

Serantes, R., F. et al. (2006) Interleukin-1beta enhances GABAA receptor cell-surface expression by a phosphatidylinositol 3-kinase/Akt pathway: relevance to sepsis-associated encephalopathy. The Journal of biological chemistry 281:14632-43.

Soh, M. S. and J. W. Lynch, Selective Modulators of alpha5-Containing GABAA Receptors and their Therapeutic Significance. Curr Drug Targets, 2015. 16(7): p. 735-46.

Tyagarajan, S. K. and J. M. Fritschy, Gephyrin: a master regulator of neuronal function? Nat Rev Neurosci, 2014. 15(3): p. 141-56.

Varley, J., et al., Clinical and experimental studies of potentially pathogenic brain-directed autoantibodies: current knowledge and future directions. J Neurol, 2015. 262(4): p. 1081-95.

Wu, Z., et al., Tonic inhibition in dentate gyrus impairs long-term potentiation and memory in an Alzheimer's [corrected] disease model. Nat Commun, 2014. 5: p. 4159.

Yee, B. K., et al., GABA receptors containing the alpha5 subunit mediate the trace effect in aversive and appetitive conditioning and extinction of conditioned fear. Eur J Neurosci, 2004. 20(7): p. 1928-36.

Zurek, A. A., et al. (2012) Inhibition of alpha5 gamma-Aminobutyric acid type A receptors restores recognition memory after general anesthesia. Anesthesia and analgesia 114:845-55.

Zurek, A. A., et al., Sustained increase in alpha5GABAA receptor function impairs memory after anesthesia. J Clin Invest, 2014. 124(12): p. 5437-41.

Savic, M. et al. (2008) Brain Research, 1208:150-159 entitled PWZ-029, a compound with moderate inverse agonist functional selectivity at GABAA receptors containing $\alpha 5$ subunits, improves passive, but not active, avoidance learning in rats Milic M. et al. (2013) Behav Brain Res, 241:206-213 entitled PWZ-029, an inverse agonist selective for a s GABAA receptors, improves object recognition, but not water-maze memory in normal and scopolamine-treated rats Forman S. A.: Clinical and molecular pharmacology of etomidate. Anesthesiology 2011; 114:695-707.

Belelli, D., et al., The interaction of the general anesthetic etomidate with the γ-aminobutyric acid type A receptor is influenced by a single amino acid. Proc Natl Acad Sci US A 94, 11031-11036 (1997).

Antunes M, Biala G: The novel object recognition memory: neurobiology, test procedure, and its modifications. Cogn Process 2012; 13:93-110.

Schindler A G, et al.: Behavioral stress may increase the rewarding valence of cocaine-associated cues through a dynorphin/kappa-opioid receptor-mediated mechanism without affecting associative learning or memory retrieval mechanisms. Neuropsychopharmacology 2010; 35:1932-42.

Herring N R, et al.: Effect of +-methamphetamine on path integration learning, novel object recognition, and neurotoxicity in rats. Psychopharmacology (Berl) 2008; 199: 637-50.

Goulart B K, et al.: Ketamine impairs recognition memory consolidation and prevents learning-induced increase in hippocampal brain-derived neurotrophic factor levels. Neuroscience 2010; 167:969-73.

Hammond R S, et al.: On the delay-dependent involvement of the hippocampus in object recognition memory. Neurobiol Learn Mem 2004; 82:26-34.

Schroder N, et al.: Neurotoxic methamphetamine regimen severely impairs recognition memory in rats. Synapse 2003; 49:89-96.

Botton P H, et al.: Caffeine prevents disruption of memory consolidation in the inhibitory avoidance and novel object recognition tasks by scopolamine in adult mice. Behav Brain Res 2010; 214:254-9.

Nanfaro F, et al.: Pregnenolone sulfate infused in lateral septum of male rats impairs novel object recognition memory. Pharmacol Rep 2010; 62:265-72.

Walf A A, et al.: Proestrous compared to diestrous wildtype, but not estrogen receptor beta knockout, mice have better performance in the spontaneous alternation and object recognition tasks and reduced anxiety-like behavior in the elevated plus and mirror maze. Behav Brain Res 2009; 196:254-60.

Aubele T, et al.: Effects of gonadectomy and hormone replacement on a spontaneous novel object recognition task in adult male rats. Horm Behav 2008; 54:244-52.

Costa M S, et al.: Caffeine prevents age-associated recognition memory decline and changes brain-derived neurotrophic factor and tyrosine kinase receptor (TrkB) content in mice. Neuroscience 2008; 153:1071-8.

Borota D, et al.: Post-study caffeine administration enhances memory consolidation in humans. Nat Neurosci 2014; 17:201-3.

Damgaard T, et al.: Positive modulation of alpha-amino-3-hydroxy-5-methyl-4-isoxazolepropionic acid (AMPA) receptors reverses sub-chronic PCP-induced deficits in the novel object recognition task in rats. Behav Brain Res 2010; 207:144-50.

Ingvar M, et al.: Enhancement by an ampakine of memory encoding in humans. Exp Neurol 1997; 146:553-9.

Tian S, et al.: Nicotine enhances the reconsolidation of novel object recognition memory in rats. Pharmacol Biochem Behav 2015; 129:14-8.

Heishman S J, et al.: Meta-analysis of the acute effects of nicotine and smoking on human performance. Psychopharmacology (Berl) 2010; 210:453-69.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

Although the present invention has been described with reference to specific features and embodiments thereof, it is evident that various modifications and combinations can be made thereto without departing from the invention. The specification and drawings are, accordingly, to be regarded simply as an illustration of the invention as defined by the appended claims, and are contemplated to cover any and all modifications, variations, combinations or equivalents that fall within the scope of the present invention.

The invention claimed is:

1. A method for treatment or prevention of impairment of memory or executive function or both in a subject, wherein said method comprises administering to the subject an agent that interrupts binding of radixin to α5GABA$_A$ receptors, wherein the agent is an isolated or synthetic peptide that binds to an α5 subunit binding domain on radixin or that binds to a radixin binding domain on an α5GABA$_A$ receptor, and wherein the isolated or synthetic peptide is 8 to 50 amino acids in length and comprises the sequence of SEQ ID NO:4, a conservative variant thereof or a sequence having at least 80% sequence identity with SEQ ID NO:4.

2. The method of claim 1, wherein the impairment of memory or executive function or both is caused by anesthesia, surgery, inflammation or trauma, Alzheimer's disease, stroke, stress, sepsis-associated encephalopathy, Down syndrome, schizophrenia, anxiety, depression, bipolar disorder or autism.

3. The method of claim 1, wherein the peptide is 8 to 40 amino acids in length.

4. The method of claim 1, wherein the peptide comprises SEQ ID NO:3, SEQ ID NO:2, SEQ ID NO:1, or a conservative variant thereof.

5. The method of claim 1, wherein the peptide additionally comprises an amino acid sequence of a cell permeation peptide that facilitates transport of the peptide across cell membranes.

6. The method of claim 1, wherein the agent is administered with a second pharmaceutically active agent.

7. The method of claim 5, wherein the cell permeation peptide that facilitates transport of the peptide across cell membranes is a cell-penetrating peptide (CPP), protein transduction domain (PTD), or spontaneous membrane translocating peptide (SMTP).

8. The method of claim 1, wherein the peptide is 8 to 20 amino acids in length.

9. A method for improving memory or executive function or both in a subject, wherein said method comprises administering to the subject an agent that interrupts binding of radixin to α5GABA$_A$ receptors, wherein the agent is an isolated or synthetic peptide that binds to an α5 subunit binding domain on radixin or that binds to a radixin binding domain on an α5GABA$_A$ receptor, and wherein the isolated or synthetic peptide is 8 to 50 amino acids in length and comprises the sequence of SEQ ID NO:4, a conservative variant thereof or a sequence having at least 80% sequence identity with SEQ ID NO:4.

10. The method of claim 9, wherein the peptide is 8 to 40 amino acids in length.

11. The method of claim 9, wherein the peptide comprises SEQ ID NO:2, SEQ ID NO:3, SEQ ID NO:4, or a conservative variant thereof.

12. The method of claim 9, wherein the peptide additionally comprises an amino acid sequence of a cell permeation peptide that facilitates transport of the peptide across cell membranes.

13. The method of claim 9, wherein the agent is administered with a second pharmaceutically active agent.

14. The method of claim 12, wherein the cell permeation peptide that facilitates transport of the peptide across cell membranes is a cell-penetrating peptide (CPP), protein transduction domain (PTD), or spontaneous membrane translocating peptide (SMTP).

15. The method of claim 9, wherein the peptide is 8 to 20 amino acids in length.

* * * * *